(12) United States Patent
Yang et al.

(10) Patent No.: US 9,846,134 B2
(45) Date of Patent: Dec. 19, 2017

(54) SPINWAVE BASED NONDESTRUCTIVE MATERIAL, STRUCTURE, COMPONENT, OR DEVICE TESTING TOOLS

(71) Applicant: NATIONAL UNIVERSITY OF SINGAPORE, Singapore (SG)

(72) Inventors: Hyunsoo Yang, Singapore (SG); Sankha Subhra Mukherjee, Singapore (SG); Jae Hyun Kwon, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 1140 days.

(21) Appl. No.: 14/020,329

(22) Filed: Sep. 6, 2013

(65) Prior Publication Data
US 2014/0097841 A1    Apr. 10, 2014

Related U.S. Application Data

(63) Continuation of application No. PCT/SG2012/000074, filed on Mar. 7, 2012.
(Continued)

(51) Int. Cl.
*G01V 3/00* (2006.01)
*G01N 24/10* (2006.01)
(Continued)

(52) U.S. Cl.
CPC .............. *G01N 24/10* (2013.01); *G01N 22/00* (2013.01); *G01R 33/60* (2013.01)

(58) Field of Classification Search
CPC .................................................... G01N 22/00
(Continued)

(56) References Cited

U.S. PATENT DOCUMENTS

| 8,779,765 B2* | 7/2014 | Grachev | H01L 45/02 324/300 |
| 9,551,686 B1* | 1/2017 | Griffith | G01N 22/00 |
| 2009/0212769 A1* | 8/2009 | Stoica | G01R 33/032 324/244.1 |

OTHER PUBLICATIONS

Bailleul, et al. "Spin waves propagation and confinement in conducting films at the micrometer scale", Europhysics Letters, 56 (5), pp. 741-747, 2001.
(Continued)

*Primary Examiner* — Louis Arana
(74) *Attorney, Agent, or Firm* — Nath, Goldberg & Meyer; Jerald L. Meyer; Tanya E. Harkins

(57) ABSTRACT

Systems and methods for spinwave-based metrology in accordance with embodiments of the disclosure involve generating and detecting spinwaves in a sample having a ferromagnetic material; and determining a material thickness, a material integrity measure, a presence of a manufacturing defect, a categorical type of manufacturing defect, and/or a manufacturing process statistic corresponding to spinwave behavior in the sample. In an embodiment, spinwaves are generated by way of concurrent exposure of a target measurement site of the sample to each of a bias magnetic field and radiation (e.g., microwave or radio frequency radiation) produced by a first set of integrated waveguides. A response signal corresponding to a behavior of spinwaves within the target measurement site can be generated by way of a second set of integrated waveguides. Various embodiments of systems and methods for generating spinwaves, detecting spinwaves, and calculating, analyzing, or monitoring one or more sample properties can be automated.

25 Claims, 26 Drawing Sheets

Related U.S. Application Data

(60) Provisional application No. 61/449,738, filed on Mar. 7, 2011.

(51) Int. Cl.
*G01N 22/00* (2006.01)
*G01R 33/60* (2006.01)

(58) Field of Classification Search
USPC .................................................. 324/300, 317
See application file for complete search history.

(56) References Cited

OTHER PUBLICATIONS

Kampen, et al. "All-Optical Probe of Coherent Spin Waves", Physical Review Letters, 88 (22), 2002.
Sakran, et al. "Localized spin-wave excitation by the evanescent microwave scanning probe", Review of Scientific Instruments, 77, 023902, 2006.
Bailleul, M., et al.,"Spin waves propagation and confinement in conducting films at the micrometer scale", Europhysics Letters, vol. 56 (5), pp. 741-747, (2001).
Sakran, F., et al., "Localized spin-wave excitation by the evanescent microwave scanning probe", Review of Scientific Instruments, vol. 77, pp. 023902-1-023902-5, (2006).
Van Kampen, M., et al. "All-Optical Probe of Coherent Spin Waves", Physical Review Letters, vol. 88, No. 22, pp. 227201-1-227201-4, (Jun. 3, 2002).
Soo-Man Seo, et al. "Current-Induced Control of Spin-Wave Attenuation", Physical Review Letters, 102, pp. 147202-1-147202-4, (Apr. 10, 2009).

\* cited by examiner

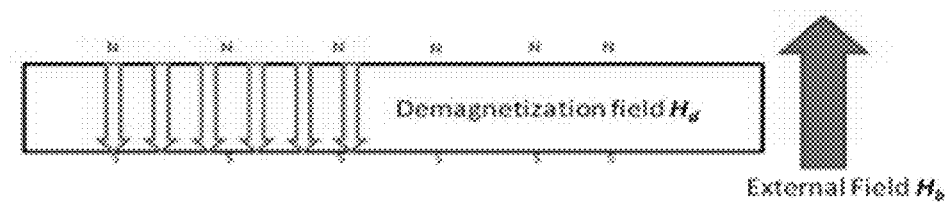
FIG. 4
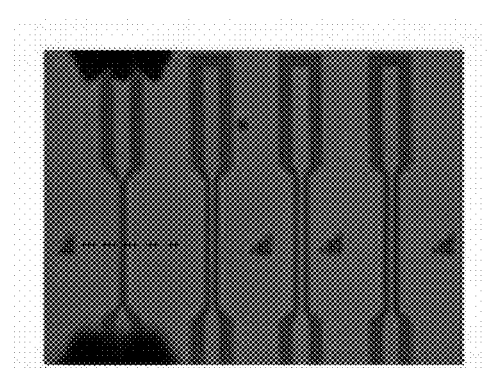 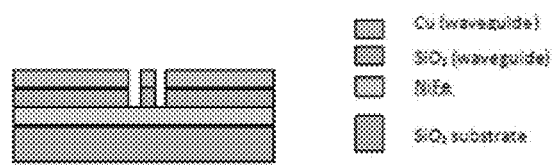
FIG. 5A  FIG. 5B

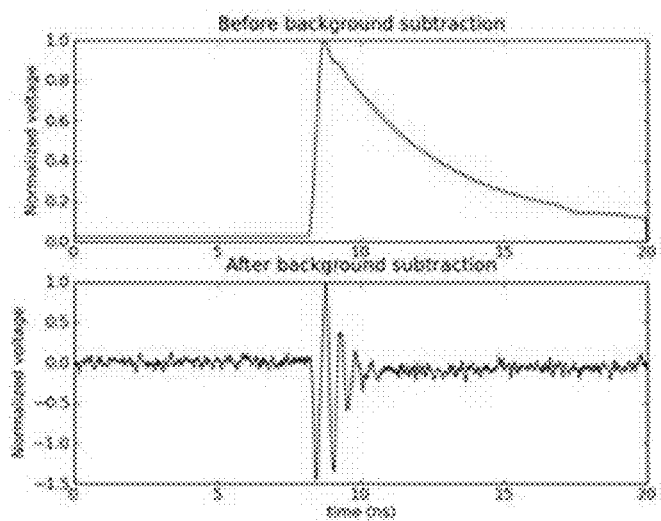
FIG. 6A
FIG. 6B
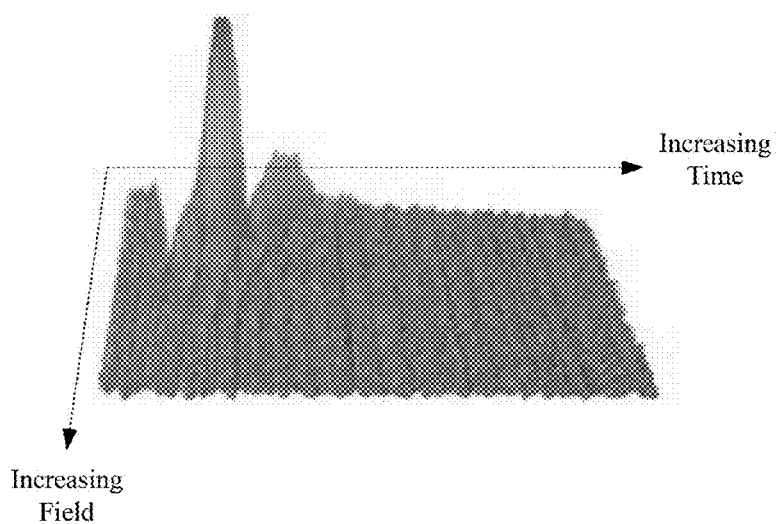
FIG. 7

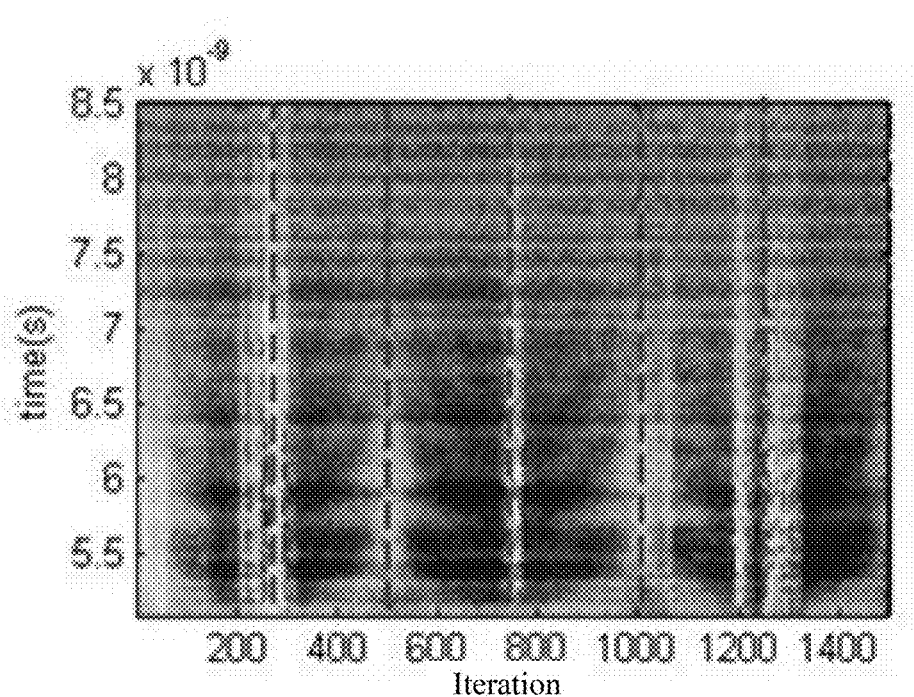
FIG. 11A
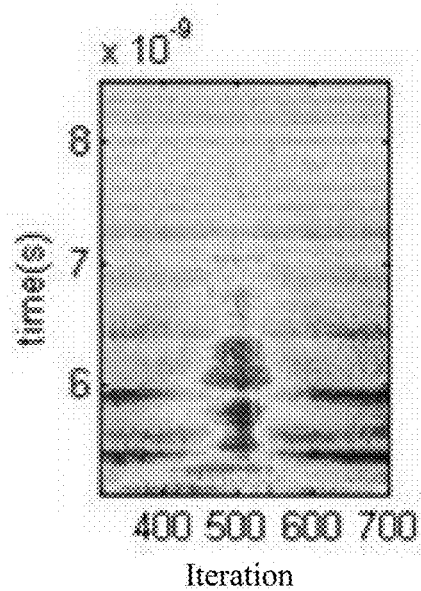 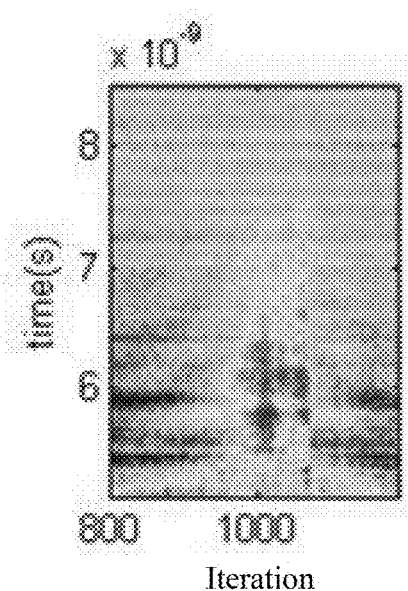
FIG. 11B  FIG. 11C

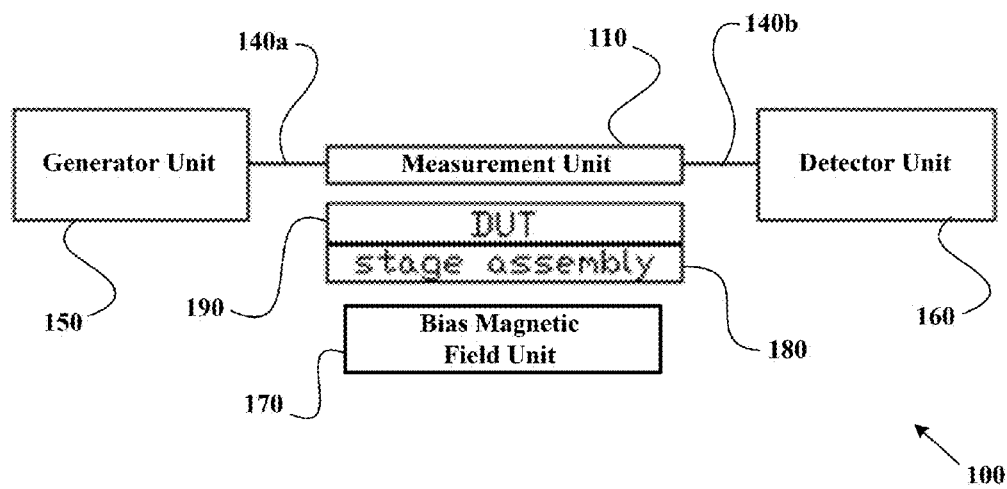
FIG. 20A
FIG. 20B
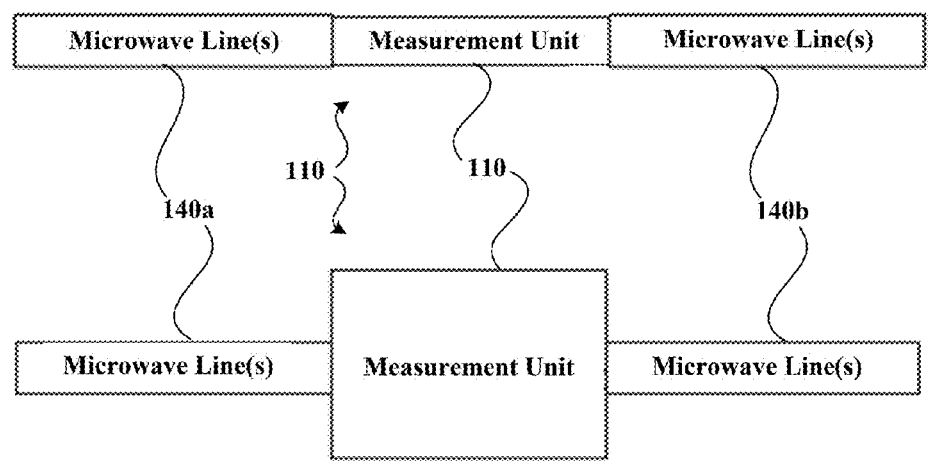
FIG. 20C

200b

200c

SPINWAVE BASED NONDESTRUCTIVE MATERIAL, STRUCTURE, COMPONENT, OR DEVICE TESTING TOOLS

CROSS REFERENCE TO RELATED APPLICATIONS

This application is a continuation of International Application Number PCT/SG2012/000074, which is incorporated by reference herein in its entirety.

TECHNICAL FIELD

The present disclosure relates generally to systems and techniques for nondestructive testing of semiconductor or other materials. More particularly, aspects of the present disclosure are directed to systems, apparatuses, circuits, and techniques for nondestructive testing or characterization of materials, structures, components, and/or devices that are encountered or produced in association with microfabrication or nanofabrication processes and which exhibit ferromagnetic properties (e.g., ferromagnetic semiconductors, magnetic metals, or magnetic insulators), where such nondestructive testing or characterization occurs by way of generating and detecting spinwaves. In a number of embodiments, generating spinwaves occurs by way of applying radio frequency or microwave radiation to such materials, structures, components, or devices; and detecting spinwaves occurs by way of detecting transmitted, reflected, and/or induced voltage signals in an associated microwave circuit.

BACKGROUND

Multiple types of thin film materials are used in the semiconductor and hard disk drive industries for a variety of purposes. The characterization of a thin film's structural properties or integrity is a necessary part of the industrial manufacture of semiconductor and hard disk drive devices. However, the characterization of thin film structural properties or integrity, particularly for certain types of thin films such as metallic films, is often challenging and frequently destructive in nature. For instance, in most industrial applications, the determination of thicknesses of ferromagnetic samples is a destructive process. Either a four-point probe is used for probing the electrical resistivity of the sample, and sample thickness is calculated from sample resistivity, or the sample is physically cleaved, and a cross-sectional image obtained, from which sample thickness is gauged. Materials characterization techniques involving destructive testing are undesirably inefficient from a materials preparation or usage standpoint, and correspondingly such techniques are expensive and/or time consuming.

Additionally, most techniques utilized for the metrology of thin films, such as ellipsometry or four-probe measurements, are generally applicable only to the measurement of continuous films. For patterned films, such as patterned structures or devices encountered in the semiconductor or hard disk drive industries, destructive testing techniques such as transmission electron microscopy (TEM) and scanning electron microscopy (SEM) are used. Furthermore, any given existing thin film metrology technique is generally quite limited with respect to the types of measurements that can be performed, and hence are undesirably limited with respect to the types of thin film characterization information they can provide.

In view of the foregoing, existing thin film characterization techniques are undesirably destructive; undesirably limited with respect to the types of material compositions or structures that can be successfully characterized; undesirably limited with respect to the types of material or structural properties that can be measured; and/or undesirably expensive or time consuming. A need exists for a metrology, measurement, or characterization technique and corresponding material, structure, component, and/or device testing tools that overcome one or more of such limitations.

SUMMARY

Embodiments in accordance with the present disclosure involve the characterization of material properties and/or the detection of defects in various types of patterned and/or un-patterned materials by way of spinwaves. Spinwaves behave much like ordinary waves, such as those that might be observed on the surface of a lake into which a pebble has been dropped, in that, they propagate along the surface of the lake, and rapidly attenuate, their energy being ultimately converted into heat. Spinwaves also rapidly attenuate. It has been recently shown that the attenuation of a spinwave may be significantly suppressed, and indeed reversed, giving rise to spinwave amplification with the help of spin-polarized current.

In general, spinwaves originate in and propagate through spinning electrons within a magnetic solid, either in the presence of an external magnetic field, or due to its own internal magnetic field. Electrons within a magnetic solid process around the magnetic field, in a manner analogous to the precession of a top due to gravity. The precession frequency depends only upon the magnetic field that each electron is immersed in, and several material properties. In magnetic solids, electrons in neighboring atoms are enjoined to one another by exchange-coupling, and are thus unable to process independent of one another. The phase-displacement among neighboring electrons, due to symmetry, are equal, just as the relative displacements of neighboring atoms within a phonon wave are equal. This gives rise to wave-like solutions of electrons precessing in a magnetic field.

Creation of a spinwave comprises first of aligning most of the electron spins in one magnetization direction, and then perturbing some of the electrons away from the direction of magnetization. These electrons start precessing, and due to exchange-coupling, proceed to drag their neighboring electrons into precession, and thus initiate a wave of precessing electrons from a point of origin. These are indeed very much real waves, and have all the properties of ordinary waves. They interfere, diffract, and transfer energy from one point to another. They propagate down magnetic circuits, and can provide valuable information about the magnetic circuit, such as information instrumental in detecting magnetic circuit defects.

Spinwaves can be generated and detected electrically, magnetically, and even optically. A prime example for electrical detection, for example, is in a magnetic random-access (MRAM) device, where the MRAM itself is capable of generating and detecting spinwaves. In non-MRAM-type applications, an external device may be used for generating and detecting spinwaves. In accordance with several embodiments of the present disclosure, external microwave sources or circuit elements can be used for the generation and detection of spinwaves, as further described in detail below. Reflected and transmitted spinwaves may be measured accurately using Hall sensors. In some embodiments, an array of such sensors can map a 2D image of a magnetic circuit. Further, using optical techniques, such as Brillouin Light Scattering (BLS) (e.g., micro-focused BLS) and time & position resolved magneto-optic Kerr effect (MOKE), in certain embodiments spinwaves can be detected or mapped in a near-continuous two-dimensional image corresponding to an entire magnetic circuit.

Spinwave-based testing in accordance with embodiments of the present disclosure enables non-destructive testing of materials, structures, components, or devices, such as semiconductor components, especially those that incorporate magnetic components. Such testing is particularly useful because it need not involve, and can entirely avoid, the fabrication of intricate Built-In Self-Test (BIST) circuits, and corresponding conventional electrical measurements made using BIST circuits. Thus, spinwave-based testing in accordance with embodiments of the present disclosure readily enables nondestructive testing and/or characterization during various portions of semiconductor fabrication processes.

For elucidating the utility of spinwave-based metrology in accordance with the present disclosure, aspects of particular representative examples are provided herein. A person of ordinary skill in the relevant art will understand that representative examples described herein are non-limiting, and many other manners of implementing spinwave-based metrology systems, apparatuses, circuits, or techniques in accordance with the present disclosure exist. Specific aspects of representative examples considered herein should not, in any way, detract from the fact that the stimulation and/or detection of spinwaves in accordance with embodiments of the present disclosure can be accomplished by way of multiple types of systems, apparatuses, components, devices, or techniques, or by way of an identical or substantially identical system, apparatus, component, device or technique exhibiting an alternate electrical configuration relative to the representative examples considered herein.

In an embodiment, spinwave-based testing includes determining or finding the high-frequency response of ground-signal-ground (GSG) or GS co-planar waveguides positioned proximate or adjacent to (e.g., on top of) a sample (e.g., a material, structure, component, or device) of interest. High-frequency signals flow along the GSG or GS lines through the dielectric material surrounding the co-planar waveguides. The characteristics of the wave propagating along the lines are acutely and ultimately determined by the nature of the material surrounding the lines. Metals having high conductivity, for example, readily absorb electric fields, and thus would result in significant signal attenuation. Dielectrics having permittivities significantly different from that of air will selectively impede certain frequency signals, and thus reshape a pulse (e.g., reshaping a square pulse to a shape that is not exactly square). The presence of a sample results in a change or deviation of effective permittivity. This change is dependent on the shape and size and characteristics of the waveguide, and is dependent upon the change in the permittivity that occurs in the surrounding dielectrics. Such characteristic differences between measurement outcomes are utilized in embodiments of the present disclosure for probing, evaluating, characterizing, testing, analyzing, or inspecting materials, structures, components, devices, or systems comprising combinations of one or more of the foregoing.

FIG. 1A is an optical image of a representative as-fabricated GSG coplanar waveguide, and FIG. 1B is a schematic illustration of a representative GSG coplanar waveguide. Coplanar waveguides can transmit high-frequency signals to and from microwave components and circuits. For creating waveguides capable of transmitting high-frequency signals in and out of the system, a waveguide needs to be appropriately designed, with knowledge of the space around the waveguide. This is because the signal travelling along the waveguide does not travel within the metallic lines, but rather the space within them, as illustrated in FIG. 2. Since the signal propagates along the space around the waveguide, most approximate equations, and even simulation tools, rely on the electrical and magnetic properties of the space surrounding the material(s) under consideration. If material or structural aspects a sample under consideration change, the "characteristic impedance" of the waveguide will also change.

FIG. 3A is a schematic illustration of one type of waveguide device 10 that can be utilized for spinwave-based metrology in accordance with an embodiment of the present disclosure. The waveguide device 10 comprises at least one waveguide 12 carried by or embedded within one or more layers of material such as a thin layer of a dielectric 14 (e.g., an oxide). On either ends of the device 10, end connectors are present that can be used for coupling to high-frequency connectors, in a manner readily understood by one of ordinary skill in the relevant art. Two connectors can be coupled to a high frequency analyzer, e.g. vector network analyzer, and S-parameters of the waveguide structure can be measured in a manner also understood by one of ordinary skill in the relevant art. Waveguides positioned or patterned proximate or adjacent to one another can alternatively or additionally be coupled to a step response measurement system. For instance, in certain embodiments, a vector network analyzer and a step response measurement system can be used simultaneously. Details of calculations relevant to spinwave-based metrology in accordance with the present disclosure for various material systems are described below. In several embodiments in accordance with the present disclosure, a sample under consideration can be mapped, scanned, or inspected by way of one or more stepper motors or piezo stages coupled to or carrying the sample and/or spinwave measurement devices or elements.

Thus, in a representative embodiment, waveguides can be fabricated that are sub-micron in size; and a spinwave-based metrology system or apparatus in accordance with the present disclosure can scan areas within a patterned chip on a wafer, and map one or more portions of a wafer (e.g., the entire, or substantially the entire wafer) on which patterned chips exist. The smaller the size of the waveguide, the smaller the size of sample that can be investigated. For instance, submicron sized waveguides can be fabricated (e.g., using e-beam lithography), and such submicron sized waveguides can be used to investigate sub-micron sized sample characteristics or features in accordance with embodiments of the present disclosure. Further, the smaller the size of the waveguides, the more the fields will be restricted to a small region around the waveguide, and hence will be more sensitive to planar technology.

When an external magnetic field is applied to exchange-coupled electrons within a ferromagnetic magnetized layer, they begin to precess, around the direction of the externally applied field. Due to the presence of exchange coupling, electrons in neighboring atoms are phase-locked, such that the phase-difference between neighboring atoms are constant, thus giving rise to spinwaves. Modes in which all electrons precess in-phase are called magneto-static standing waves, and are said to exhibit uniform precession modes. In bulk, there is only one precession mode for a particular value of magnetic field. However, in the case of thin films, the modes are quantized. The electrons at the edge of the solid are unable to precess because of the existence of surface energies. This results in the quantization of standing waves within or along the thickness of the sample.

Noninvasive spinwave-based metrology techniques in accordance with various embodiments of the present disclosure methodology are based upon the phenomena of spinwaves and ferromagnetic resonance (FMR), and rely upon interaction between the application of microwave energy or radiation to a ferromagnetic sample and the magnetism of the ferromagnetic sample. Such microwave energy can be applied by way of one or more waveguide structures. For time varying (e.g., sinusoidal) signals applied to one or more waveguide structures, microwave energy can be most-effectively coupled into the aforementioned quantized magnetization modes when the frequency of the applied signal matches that of a particular standing wave magnetization mode.

In accordance with various embodiments of the present disclosure, ferromagnetic resonance measurements of thin-film samples, involving the observing the absorption intensity of absorbed microwave power relative to one or more applied, external, or extrinsic magnetic fields, can be readily and practicably accomplished in an industrial or manufacturing environment by way of a time-resolved measurement technique involving the use of patterned, integrated, or coplanar waveguides. In one such technique, a time varying signal, pulse, or wave (e.g., a square wave) is applied to one end of a coplanar waveguide, resulting in the generation of microwave radiation that propagates along the waveguide. The rising/falling-edge of the pulse causes the instantaneous applied magnetization vector of a sample exposed to such microwave radiation to change. This change results in the precession of the electrons about a new direction. Due to damping however, the magnetization will eventually settle into the direction of the external magnetic field. The resultant electrical signal that results from such damped oscillations is one of a damped sinusoid, as shown in FIG. 3B. The frequency of oscillation depends upon the effective magnetic field, while the exponential decay depends upon a damping constant. For a particular ferromagnetic material, for a constant applied field, the thickness of the film can be ascertained from a difference between fundamental and 2nd order precessional frequencies. Spinwave-based metrology techniques in accordance with embodiments of the present disclosure are useful for various purposes, including estimating, analyzing, or measuring at least the following physical information, qualities, parameters, or data:

(a) The thickness of ferromagnetic films or structures;
(b) local thickness variations in ferromagnetic films or structures; and
(c) the presence or nature of manufacturing defects, such as patterning defects.

Thin ferromagnetic film materials have been used in the disk drive industry as well as the semiconductor industry for various purposes. The characterization of the structural integrity of thin film materials, especially metallic thin films, is often challenging, and conventional characterization is generally destructive in nature. Conventional characterization is an expensive procedure, and by way of embodiments in accordance with the present disclosure, conventional destructive characterization can be avoided or eliminated altogether. Furthermore, most conventional thin film metrology techniques, such as ellipsometry or four probe measurements, are generally only applicable for the measurement of continuous films. For patterned structures, such as those used in the semiconductor and the HDD industry, destructive testing such as TEM and SEM are used. Spinwave-based metrology techniques in accordance with embodiments of the present disclosure are applicable to industries or industrial production environments that utilize materials having ferromagnetic films, layers, such as hard disk drive (HDD), magnetic random access memory (MRAM), and spintronics device manufacturing. Spinwave-based metrology techniques in accordance with embodiments of the present disclosure can do at least the following:

(a) measure the structural integrity of patterned and un-patterned films;
(b) measure the existence and/or nature of irregularities or defects in patterned films;
(c) identify or determine the type of thin film material or discriminate between different thin film materials for both patterned and un-patterned films; and
(d) determine the thickness of patterned and un-patterned films using spinwave resonance.

Such physical qualities are measured by three different characteristics of the spinwaves and FMR spectra, and are largely independent of one another. Furthermore, one will be hard-pressed to find a conventional metrology or measurement technique that in itself is able to provide all of the information above. Furthermore, in accordance with various embodiments of the present disclosure, not only is the determination of sample properties non-destructive, the accuracy of the spinwave-based metrology technique increases as the thickness of the sample decreases.

In accordance with an aspect of the present disclosure, a metrology process includes exciting spinwaves within a target measurement site of a sample; detecting at least one behavior of the spinwaves excited within the target measurement site; and automatically generating a target measurement site dataset based upon detecting the at least one behavior of the spinwaves excited within the target measurement site, the target measurement site dataset corresponding to at least one of a material thickness, a material integrity measure, a presence of a manufacturing defect, and a categorical type of manufacturing defect. Exciting spinwaves and/or detecting at least one behavior of the spinwaves excited within the target measurement site can occur in one or more manners, for instance, by way of patterned or integrated structural elements such as waveguides. Each of exciting spinwaves, detecting at least one behavior of the spinwaves, and automatically generating a target measurement site dataset can be automatically repeated for a plurality of (a) target measurement sites of the sample, and/or (b) samples.

In accordance with a further aspect of the present disclosure, a metrology system includes a first apparatus, device, or structure configured for exciting spinwaves within a target measurement site of a sample; a second apparatus, device, or structure configured for detecting at least one behavior of spinwaves excited within the target measurement site of the sample; and a processing system configured for automatically generating a target measurement site dataset based upon detecting the at least one behavior of the spinwaves excited within the target measurement site, the target measurement site dataset corresponding to at least one of a material thickness, a material integrity measure, a presence of a manufacturing defect, and a categorical type of manufacturing defect.

The first apparatus can include, for instance, a signal generation unit coupled to a first set of patterned or integrated structural elements such as integrated waveguides; and the second apparatus can include, for instance, a signal detection unit coupled to a second set of patterned or integrated structural elements such as integrated waveguides. The processing system can include system control, signal detection, processing, and/or analysis resources, such as one or more signal processing units or devices, microcontrollers, state machines, computing devices, or computer systems, and memory/information storage resources, computer readable media associated therewith, and corresponding sets of program instructions that, when executed, perform one or more metrology, measurement, or testing processes in accordance with embodiments of the present disclosure. The system can further include a positioning apparatus configured for establishing a relative positioning between the sample and at least one of the first apparatus and the second apparatus. The positioning apparatus can include, for instance, an automated stage or stage assembly that can spatially position the sample with respect to x, y, z, and/or θ axes or directions.

The first apparatus, the second apparatus, the processing system, and the positioning apparatus can be configured for automatically generating a plurality of target measurement site datasets corresponding to a plurality of target measurement sites within the sample, each target measurement site dataset within the plurality of target measurement site datasets corresponding to at least one of a material thickness, a material integrity measure, a presence of a manufacturing defect, and a categorical type of manufacturing defect for a target measurement site within the plurality of target measurement sites. Additionally or alternatively, the first apparatus, the second apparatus, the processing system, and the positioning apparatus can be configured for automatically generating a plurality of target measurement site datasets corresponding to a plurality of samples, each target measurement site dataset within the plurality of target measurement site datasets corresponding to at least one of a material thickness, a material integrity measure, a presence of a manufacturing defect, and a categorical type of manufacturing defect for a sample within the plurality of samples.

In accordance with an aspect of the present disclosure, a metrology process includes providing a sample; providing a first bias magnetic field; generating first radiation by way of a first set of patterned structural elements, the first set of patterned structural elements fabricated in accordance with microfabrication techniques and/or nanofabrication techniques; concurrently exposing a first target measurement site of the sample to the first bias magnetic field and the first radiation to thereby excite spinwaves within the first target measurement site; and detecting a first response signal corresponding to a behavior of the spinwaves excited within the first target measurement site. The first radiation can include microwave radiation, radio frequency radiation, or radiation characterized by another wavelength or frequency (e.g., millimeter wave radiation). The first set of patterned structural elements can include, for instance, a first set of waveguides.

Detecting the first response signal can include generating an electrical signal carried by a second set of patterned structural elements, the electrical signal carried by the second set of patterned circuit elements corresponding to a manner in which the spinwaves excited within the first target measurement site interact with the first radiation generated by the first set of patterned structural elements. The second set of patterned structural elements can include, for instance, a second set of waveguides. The first set of waveguides and the second sets of waveguides can be physically distinct or physically non-distinct.

Detecting the first response signal can include detecting radiation transmitted through the sample; detecting radiation reflected by the sample; and/or generating a voltage in the second set of patterned structural elements by way of magnetic induction corresponding to the behavior of spinwaves within the first target measurement site.

The foregoing process can also include calculating time-domain and/or frequency-domain aspects of the first response signals; and determining at least one of a material thickness, a material integrity measure, a presence of a manufacturing defect, a categorical type of manufacturing defect, and a manufacturing process statistic corresponding to the behavior of spinwaves within the first target measurement site.

The above process can additionally include providing a second bias magnetic field; concurrently exposing the first target measurement site of the sample to the first bias magnetic field and one of the first radiation and second radiation generated by the first set of patterned structural elements to thereby excite spinwaves within the first target measurement site; and detecting a second response signal corresponding to a behavior of the spinwaves excited within the first target measurement site.

Furthermore, the process can include displacing the sample; exposing a second target measurement site of the sample to one of the first bias magnetic field and a second bias magnetic field concurrent with exposing the second target measurement site of the sample to one of the first radiation and second radiation generated by the first set of patterned structural elements to thereby excite spinwaves within the second target measurement site; and detecting a second response signal corresponding to a behavior of the spinwaves excited within the second target measurement site. Displacing the sample can include displacing the sample while the first set of patterned structural elements remains stationary and/or displacing the first set of patterned structural elements while the sample remains stationary.

In accordance with another aspect of the present disclosure, a metrology process includes providing a sample; providing a first bias magnetic field; generating first radiation; concurrently exposing a first target measurement site of the sample to the first bias magnetic field and the first radiation to thereby excite spinwaves within the first target measurement site; and detecting a first response signal corresponding to a behavior of the spinwaves excited within the first target measurement site by way of a first set of patterned structural elements, the first set of patterned structural elements fabricated in accordance with microfabrication and/or nanofabrication techniques. The first radiation can include microwave radiation, radio frequency radiation, or other radiation (e.g., characterized by a different wavelength/frequency). The first set of patterned structural elements can include a first set of waveguides.

Detecting the first response signal can include generating an electrical signal carried by the first set of patterned structural elements, the electrical signal carried by the first set of patterned circuit elements corresponding to a manner in which the spinwaves excited within the first target measurement site interact with the first radiation.

Depending upon embodiment details, detecting the first response signal can include detecting radiation transmitted through the sample, detecting radiation reflected by the sample, and/or generating a voltage in the first set of patterned structural elements by way of magnetic induction corresponding to the behavior of spinwaves within the first target measurement site.

In a manner identical or analogous to that described previously, the process can include calculating at least one of time-domain and frequency-domain aspects of the first response signals; and determining at least one of a material thickness, a material integrity measure, a presence of a manufacturing defect, a categorical type of manufacturing defect, and a manufacturing process statistic corresponding to the behavior of spinwaves within the first target measurement site. Correspondingly, the process can also include providing a second bias magnetic field; concurrently exposing the first target measurement site of the sample to the first bias magnetic field and one of the first radiation and second radiation to thereby excite spinwaves within the first target measurement site; and detecting a second response signal by way of the first set of patterned structural elements, the second response signal corresponding to a behavior of the spinwaves excited within the first target measurement site. Moreover, the process can include displacing the sample; exposing a second target measurement site of the sample to one of the first bias magnetic field and a second bias magnetic field concurrent with exposing the second target measurement site of the sample to one of the first radiation and second radiation to thereby excite spinwaves within the second target measurement site; and detecting by way of the first set of patterned structures a second response signal corresponding to a behavior of the spinwaves excited within the second target measurement site.

In accordance with an aspect of the present disclosure, a metrology apparatus includes a bias magnetic field unit configured for providing a set of bias magnetic fields; a first set of patterned structural elements configured for providing radiation within a spatial spinwave generation region, the first set of patterned structural elements fabricated in accordance with microfabrication techniques and/or nanofabrication techniques; a sample stage configured for carrying a sample such that a first target measurement site of the sample is disposable within the spatial spinwave generation region; and a response signal generation apparatus configured for generating a response signal corresponding to a behavior of spinwaves generated within the first target measurement site of the sample.

The apparatus can further include a set of signal generators. The first set of patterned structural elements can include a first set of waveguides coupled to the set of signal generators. The first set of waveguides can include a plurality of electrically distinct waveguides coupled to the set of signal generators. For instance, in one configuration, a switching unit is configured for coupling a plurality of electrically distinct waveguides within the first set of waveguides to a single signal generator. In another configuration, the set of signal generators comprises a plurality of signal generators.

The response signal generation apparatus is configured for detecting radiation transmitted through the sample, detecting radiation reflected from the sample, and/or generating a voltage signal by way of magnetic induction in response to a behavior of spinwaves within the first target measurement site. In an embodiment, the response signal generation apparatus includes a second set of patterned structural elements, such as a second set of waveguides, fabricated in accordance with one of microfabrication techniques and nanofabrication techniques. The second set of waveguides can include a plurality of electrically distinct waveguides. Also, the first set of waveguides and the second set of waveguides can include an identical number of electrically distinct waveguides.

The sample stage can be configured for displacing the sample to position a second target measurement site of the sample within the spatial spinwave generation region. Alternatively, the apparatus can include a displacement apparatus configured for displacing the set of patterned structural elements while the sample remains stationary.

In accordance with another aspect of the present disclosure, a metrology apparatus includes a bias magnetic field unit configured for providing a set of bias magnetic fields; a radiation generation apparatus configured for providing radiation within a spatial spinwave generation region; a sample stage configured for carrying a sample such that a first target measurement site of the sample is disposable within the spatial spinwave generation region; and a first set of patterned structural elements configured for generating a response signal corresponding to a behavior of spinwaves within the first target measurement site, the first set of patterned structural elements fabricated in accordance with microfabrication techniques and/or nanofabrication techniques. The sample stage can be configured for displacing the sample to position a second target measurement site, a third target measurement site, and/or another target measurement site of the sample within the spatial spinwave generation region.

The first set of patterned structural elements can include a first set of waveguides coupled to a set of electrical signal detectors, and the first set of waveguides can include a plurality of electrically distinct waveguides. The apparatus can also include a switching unit coupling a plurality of electrically distinct waveguides within the first set of waveguides to a single electrical signal detector. Alternatively, the set of electrical signal detectors can include a plurality of electrical signal detectors.

The first set of patterned structural elements is configured for detecting radiation transmitted through the sample, detecting radiation reflected from the sample, and/or generating a voltage signal by way of magnetic induction in response to a behavior of spinwaves within the first target measurement site.

In some embodiments, the radiation generation apparatus includes a second set of patterned structural elements, such as a second set of waveguides, fabricated in accordance with microfabrication techniques and/or nanofabrication techniques. The second set of waveguides can include a plurality of electrically distinct waveguides. Additionally, the first set of waveguides and the second set of waveguides have an identical number of electrically distinct waveguides.

BRIEF DESCRIPTION OF THE DRAWINGS

FIG. 4 is a schematic illustration of an external magnetic field $H_b$ applied across a sample, which produces north (N) and south (S) poles across faces of the sample.

FIG. 5A is an image of an embodiment of a GSG waveguide structure fabricated or patterned on top of a test sample.

FIG. 5B is a schematic cross sectional illustration of the GSG waveguide structure of FIG. 5A.

FIG. 6A depicts a normalized signal obtained at one end of a 75 nm waveguide structure corresponding to FIG. 5A when an impulse signal was applied at the other end of the waveguide structure.

FIG. 6B illustrates aspects of extracting an FMR signal.

FIG. 7 is a plot of a representative FMR signal as a function of applied bias magnetic field.

FIG. 11A is a contour plot of time-domain spinwave measurements directed to detecting partial etching in the ferromagnetic pattern of FIG. 10A.

FIGS. 11B-11C are time-domain spinwave measurements directed to detecting partial etching in the ferromagnetic pattern of FIG. 10A.

FIGS. 20A-D are schematic illustrations showing portions of a spinwave-based metrology or measurement system, apparatus, or device 100 in accordance with an embodiment of the present disclosure.

DETAILED DESCRIPTION

Figure 1A:
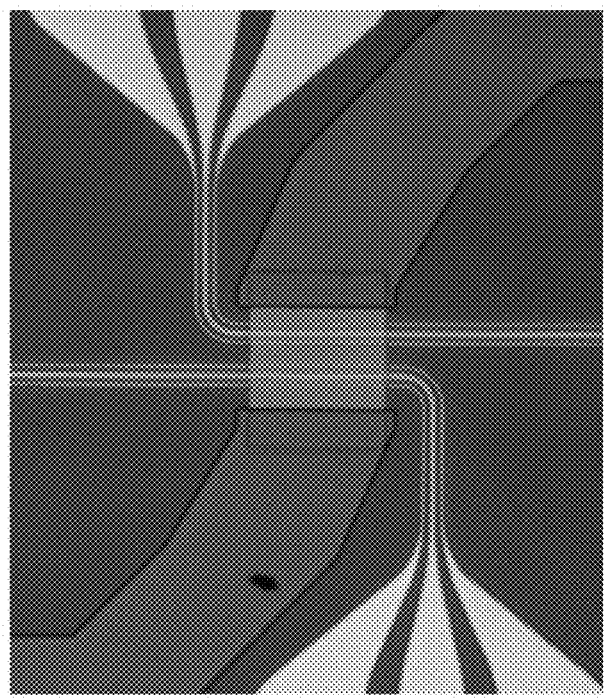
FIG. 1A is an optical image of a representative as-fabricated GSG coplanar waveguide.
Figure 1B:
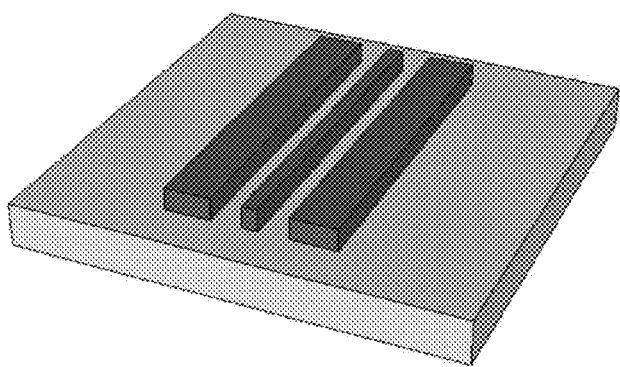
FIG. 1B is a schematic illustration of a representative GSG coplanar waveguide.
Figure 2:
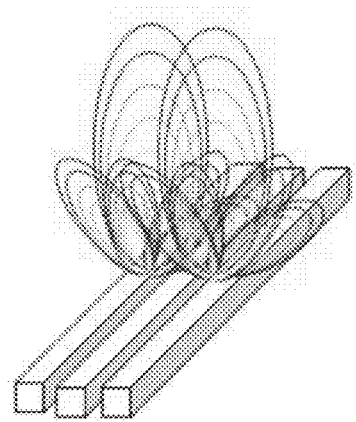
FIG. 2 is a schematic illustration of a signal generated or traveling within a spatial region between waveguides.
Figure 3A:
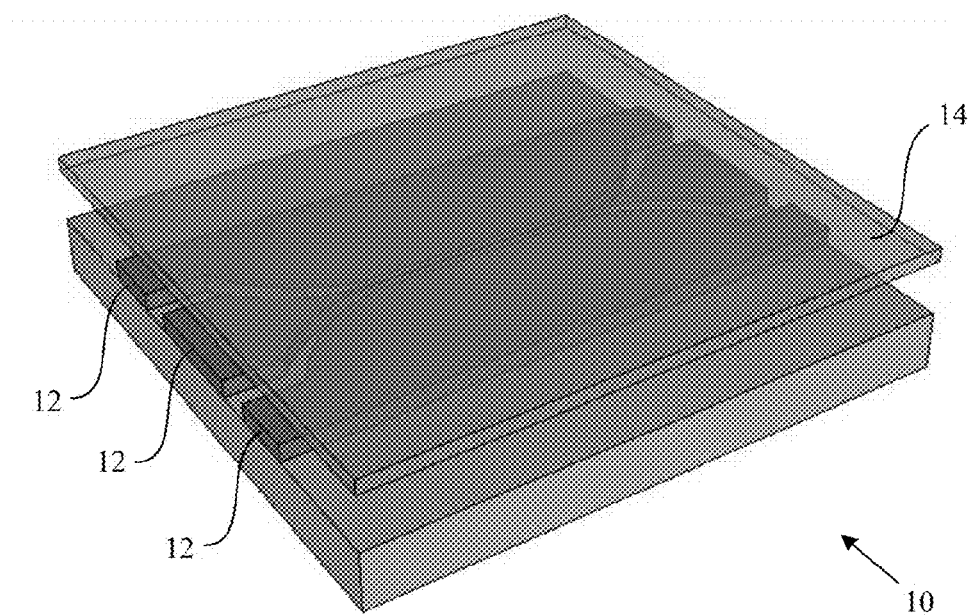
FIG. 3A is a schematic illustration of a type of waveguide device that can be utilized for spinwave-based metrology in accordance with an embodiment of the present disclosure.
Figure 3B:
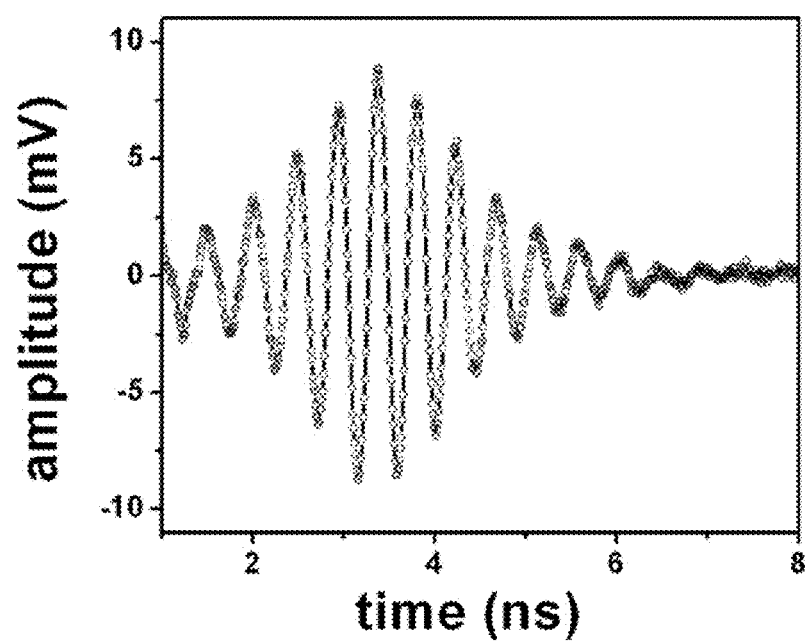
FIG. 3B is a graph showing damped spinwave oscillations corresponding to damped sinusoidal behavior.

In the present disclosure, the depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in the description herein implies "and/or" unless specifically indicated otherwise.

As used herein, the term "set" corresponds to or is defined as a non-empty finite organization of elements that mathematically exhibits a cardinality of at least 1 (i.e., a set as defined herein can correspond to a singlet or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, a structural feature, an object, a process, a physical parameter, or a value depending upon the type of set under consideration.

As further detailed herein, embodiments in accordance with the present disclosure are directed to systems, apparatuses, circuits, and techniques for the nondestructive/noncontact probing, evaluation, characterization, measurement, testing, analysis, and/or inspection of materials, structures, components, and/or devices that (1) are encountered or produced in association with microfabrication or nanofabrication processes (e.g., microscale fabrication processes involving micron-size characteristic feature sizes, geometries, or linewidths, and nanoscale fabrication processes involving nanometer-size characteristic feature sizes, geometries, or linewidths); and which (2) exhibit magnetic field dependent behavior or properties, for instance, magnetic field dependent electrical properties such as ferromagnetic properties. In various embodiments, such materials, structures, components, or devices include ferromagnetic semiconductor materials, for instance, ferromagnetic materials used in the manufacture of hard disk drives (HDD), magnetic random access memory (MRAM), or spintronic circuits.

Nondestructive testing in accordance with embodiments of the present disclosure occurs by way of (1) the generation of spinwaves; and (2) the detection of spinwaves or spinwave-related phenomena or effects. In a number of embodiments, the generation of spinwaves involves exposing a set of materials, structures, components, or devices under consideration to (a) one or more magnetic fields, such as a set of applied, external, or extrinsic magnetic fields; and (b) radio frequency or microwave energy or radiation produced by way of integrated or patterned circuit elements, for instance, ground-signal-ground (GSG) and/or ground-signal (GS) probes, waveguides, or integrated circuit patterns, as further detailed below. The detection of spinwaves involves detecting, sensing, or measuring particular signals, signal parameters, and/or circuit parameters that exist or arise as a consequence of the aforementioned spinwave generation. In multiple embodiments, the detection of spinwaves occurs by way of detecting in one or more portions of an electrical circuit, such as a radio frequency or microwave circuit configured for applying or delivering microwave radiation to material(s), structure(s), component(s), or device(s) under consideration and generating spinwaves therein, spinwave-related effects, such as voltage signals induced, as a consequence of the generation of spinwaves in the material(s), structure(s), component(s), or device(s) under consideration.

For purpose of brevity and clarity, in various portions of the following description nondestructive probing, evaluation, characterization, measurement, testing, analysis, and/or inspection in accordance with embodiments of the present disclosure is simply referred to as "nondestructive testing." Nondestructive testing by way of spinwaves or spinwave-related effects can be referred to as spinwave or spinwave-based metrology, measurement, probing, testing, characterization, analysis, or inspection. Furthermore, while various portions of the following disclosure describe the use of microwave signals/microwave radiation, one of ordinary skill in the relevant art will understand that multiple embodiments of spinwave metrology or measurement systems, apparatuses, or circuits in accordance with the present disclosure can be designed to operate using signals and radiation of other frequencies, such as radio frequency signals/radio frequency radiation, or millimeter wave signals/millimeter wave radiation.

Aspects of Representative Measurements/Properties Using Spinwave Metrology

Determination of Ferromagnetic Film Thickness

The measurement or estimation of ferromagnetic film thickness involves two phenomena, namely (a) a demagnetization field in thin ferromagnetic samples; and (b) precessional motion experienced by electrons in the thin ferromagnetic film when their magnetic moments are disturbed from the direction of an applied magnetic field. A thin ferromagnetic sample, when exposed to or placed in an external magnetic field $H_b$, develops poles across its two faces along a direction parallel to the magnetic field. This results in a field within the ferromagnetic sample, which is referred to as a demagnetization field $H_d$. The demagnetization field $H_d$ tends to reduce the overall magnetic field within the ferromagnetic sample by the magnitude demagnetization field $H_d$, as schematically represented in FIG. 4. The demagnetization field $H_d$ is proportional to the applied field and the inverse of the sample thickness.

The precessional frequency of electrons slightly perturbed from their equilibrium position can be determined based upon Kittle's formula for FMR frequency, as follows:

$$\omega_p = \gamma \mu_0 \sqrt{M_S(H_k + H_b)} \quad (1)$$

where, $\omega_p$ is the precessional angular frequency of the magnetic moments, $\gamma$ is the gyromagnetic ratio, $\mu_0$ is the permittivity of free space, $M_S$ is the saturation magnetization of the sample under study, $H_k$ is an anisotropy field of the sample, and $H_b$ is the applied magnetic field.

In a thin ferromagnetic sample, due to the demagnetization field, the applied field gets reduced, by a factor that is the inverse of the thickness of the thickness of the sample. Thus, the field within the sample can be written as follows:

$$H_i = H_b - H_d = H_b - \alpha_1 \frac{1}{t_{sample}} H_b \quad (2)$$

where $\alpha_1$ is a factor that relates the applied field to the demagnetization field. Noting that the precessional angular frequency ($\omega_p$) and the precessional frequency ($f_p$) are related as $\omega_p = 2\pi f_p$, Equations (1) and (2) can be combined to obtain an expression for the FMR as follows:

$$f_p^2 = \left[\frac{\gamma^2 \mu_0^2}{4\pi^2} M_s\right]\left\{1 - \alpha_1 \frac{1}{t_{sample}}\right\} H_b + \left(\frac{\gamma^2 \mu_0^2}{4\pi^2} M_s H_k\right). \quad (3)$$

As can be seen from Equation (3), the square of the FMR frequency is linearly related to the applied bias magnetic field. Furthermore, the slope of this linear relationship depends upon the inverse of the sample thickness. Thus, the thickness of a sample can be directly determined from the slope of the FMR spectra.

Aspects of a Representative Sample Thickness Measurement Technique

FIG. 5A is an image of an embodiment of a GSG waveguide structure fabricated or patterned on top of a test sample. FIG. 5B is a schematic cross sectional illustration of the GSG waveguide structure of FIG. 5A, corresponding to a cross section through the dashed line in FIG. 5A. Experimental measurements of sample thicknesses performed by way of spinwave-based metrology in accordance with the present disclosure involved the deposition of ferromagnetic sample films/patterns of different thicknesses on top of a glass film, layer, substrate, or carrier. More particularly, NiFe film samples having thicknesses of 100 nm, 75 nm, 30 nm, and 20 nm (e.g., as measured by material deposition time in view of a known or previously calibrated deposition rate) were deposited. On top of these sample films, Cu waveguides (e.g., such as shown in FIG. 5A) were deposited, separated from the NiFe film by an insulating layer of $SiO_2$, as schematically illustrated in FIG. 5B (which mimics or corresponds to portions of a magnetic device, in a manner recognizable by one of ordinary skill in the relevant art).

Electrical measurements were performed by probing the two ends of the waveguide structure by high-frequency ground-signal-ground (GSG) probes (a set of which can be seen in at the left-most waveguide in FIG. 5A). A 2V, 400 ps pulse was applied at one end of the waveguide by a high-frequency pulse generator, and its response measured at the other end, by a high-frequency real-time oscilloscope. During the measurement, a known magnetic field (the bias field) was applied across the sample in the out-of-plane direction.

When a bias field is applied, the magnetic moments of most electrons align along the direction of the field. When these electrons are perturbed slightly from their mean position, they do not immediately align themselves back to their original positions, but rather precess about the direction of magnetization and slowly align themselves in the direction of the field after a characteristic time determined by the damping of the material. The frequency at which these moments precess is shown in Equation (1). These precessions induce voltages about any electrical or circuit loops present in accordance with Faraday's law of induction, including the electrical loop corresponding to the waveguide structure. Voltages induced from these precessions are superimposed on the pulse travelling along the waveguide, and can be extracted by subtracting the background voltage from the signals.

FIG. 6A depicts a normalized signal obtained (using an oscilloscope) at one end of the waveguide structure of FIG. 5A for the 75 nm waveguide structure when an impulse signal was applied at the other end of the waveguide structure. This signal is superimposed with the induced voltage signal resulting from the precession of the magnetic moments of the electrons, which can be extracted as shown in FIG. 6B.

The FMR signal is obtained by subtracting the signal that is measured during the application of the highest bias magnetic field (5952 Oe) from that obtained at all other applied bias magnetic fields. As can be observed from Equation (1), the frequency of the FMR signal increases with applied field. The increase in signal frequency with increasing bias is plainly apparent in corresponding FIG. 7, which depicts the FMR signal as a function of applied bias magnetic field. Once the FMR signal is obtained as a function of the applied bias field, a fast-Fourier transform (FFT) is performed. The FMR frequency can be obtained from the FFT spectra.

Figure 8:
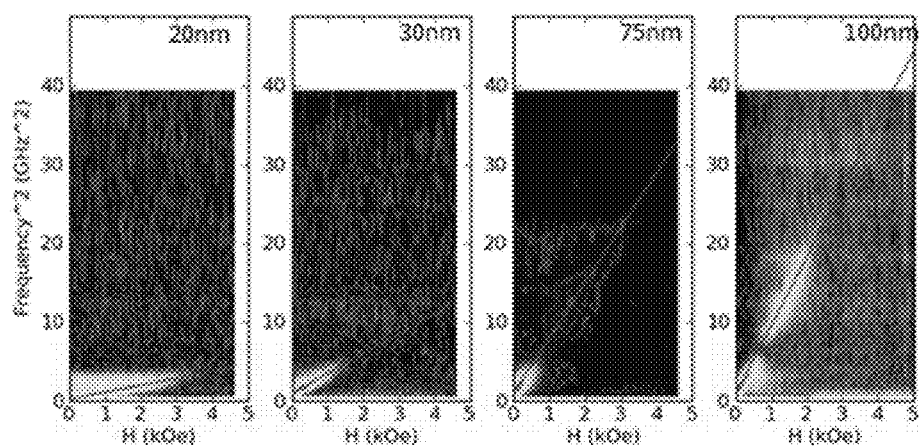
FIG. 8 shows FFT contour plots of FMR signals plotted as a function of the square of FMR frequency (y-axis) and the applied bias magnetic field (x-axis).

FIG. 8 shows FFT contour plots of FMR signals obtained for the samples under consideration, plotted as a function of the square of the FMR frequency (y-axis) and the applied bias magnetic field (x-axis). Solid lines on the plots indicate an approximate linear relationship between the square of the frequency of FMR precessions, and the bias field, as predicted by Equation (1).

As can be seen from FIG. 8, the slopes of such solid lines decrease in magnitude as the thickness of the samples decreases, which is predicted by Equation (1). All quantities in Equation (1) are physical constants, other than $M_s$, $H_b$, $\alpha_1$, and $H_k$. Using a nominal value of 840 kA/m (obtained from literature) for the saturation magnetization, the prefactor to the slope ($\gamma^2 \mu_0^2 M_s / 4\pi^2$) in Equation (1) is calculated to be $1.039 \times 10^{15}$ Hz$^2$/(A/m). Thus, the thickness-dependence of the slope, $1 - \alpha_1 / t_{sample}$, may be plotted as a function of the inverse of the sample thickness, to obtain $\alpha_1$.

Figure 9A:
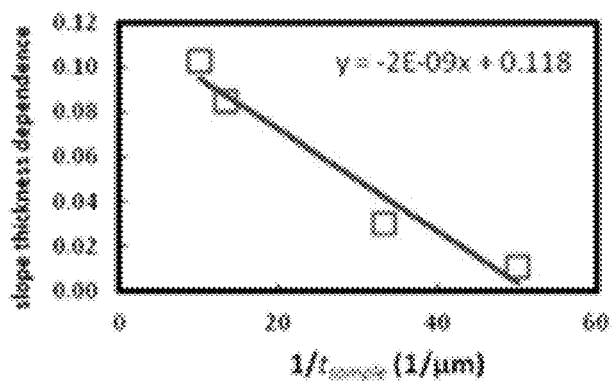
FIG. 9A is a plot showing the dependence of slopes indicated in FIG. 8 on inverse sample thickness.
Figure 9B:
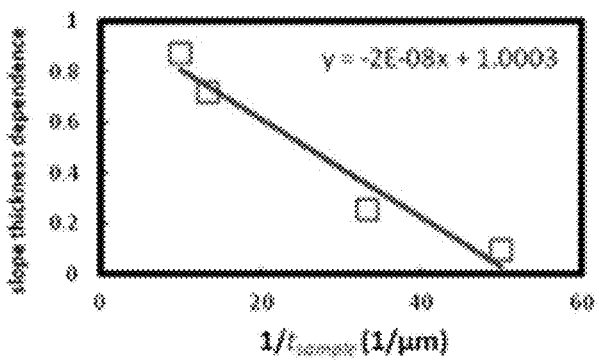
FIG. 9B is an error corrected plot corresponding to FIG. 9A.

FIG. 9A is a plot showing the dependence of the slope on inverse sample thickness, and FIG. 9B is a corresponding plot following error correction. FIGS. 9A and 9B additionally illustrate linear fits to obtained sample data, and corresponding equations. More particularly, FIG. 9A is a plot showing the thickness dependence of the slope $(1 - \alpha_1 / t_{sample})$ as a function of $(1/t_{sample})$. Note that for $1/t_{sample} = 0$, corresponding to a bulk sample, the line should theoretically reach 1. However, as FIG. 9A shows, the line actually intersects a point that has a value of 0.118, which can be defined as a factor by which the value of saturation magnetization is in error. Such an error can be easily corrected by making the value of the saturation magnetization equal to 99.12 kA/m, and repeating the calculations. The corresponding updated or error corrected plot is shown in FIG. 9B.

Aspects of a Representative Etching Irregularity Detection Technique

A direct result of the relationship between the FMR response and the thickness of ferromagnetic films is that etching irregularities such as partial etching of samples can be directly detected from measurements made in accordance with embodiments of the present disclosure (e.g., sample thickness measurements such as described above). Partial etching is a major fault mechanism in MRAM and bit pattern HDD media. The samples under consideration for the detection of partial etching included films having two thicknesses. Thus, two different frequencies are directly measureable from experiments similar to the ones described above.

Figure 10A:
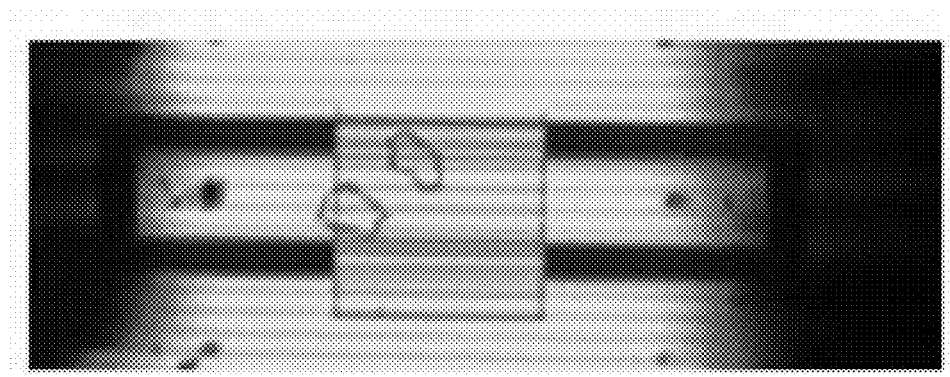
FIG. 10A is an image of a GSG waveguide having a square ferromagnetic pattern or patterned layer in a center portion of the waveguide, where linear grooves have been etched into the ferromagnetic patterned layer.

FIG. 10A is an image of a GSG waveguide having a square ferromagnetic patterned layer in a center portion of the waveguide, where linear grooves have been etched into the ferromagnetic patterned layer. A representative applied bias magnetic field used in performing spinwave measurements directed to detecting partial etching is shown in FIG. 10B.

Figure 10B:
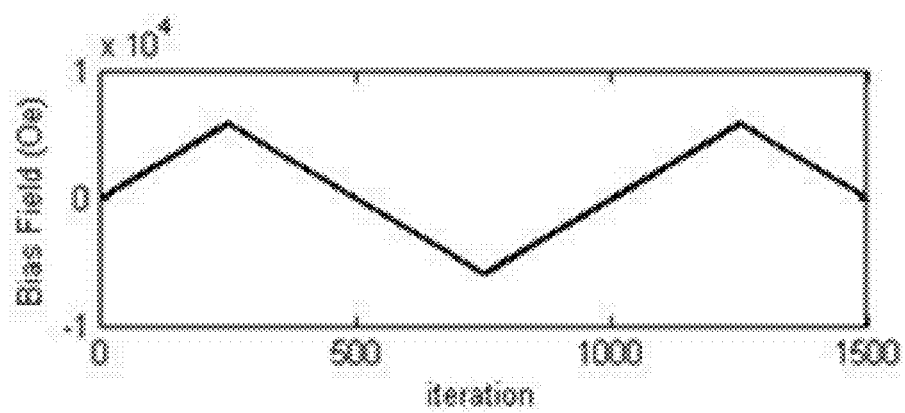
FIG. 10B is a representative applied bias magnetic field used in performing spinwave measurements directed to detecting partial etching in the GSG waveguide of FIG. 10A.

In the partial etching detection experiments, an out-of-plane bias field was swept across the device in the manner indicated in FIG. 10B. FIG. 11A is a contour plot of corresponding time-domain measurements. Symmetry points in the measurements should be apparent approximately every 250th iteration, because the coercivity of NiFe in the out-of-plane direction is very small. Such symmetry points are indicated in FIG. 11A by vertical dashed lines. From corresponding FIGS. 11B and 11C, the interference patterns between two different frequencies are clearly visible.

Figure 12:
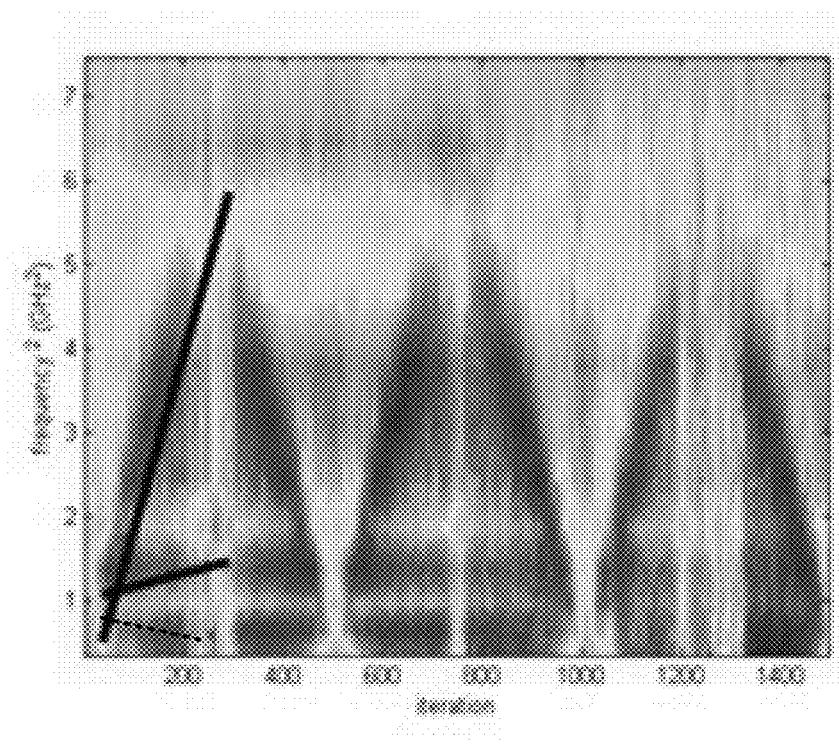
FIG. 12 is a plot of the frequency of measured time domain signals as a function of iteration, corresponding to spinwave measurements directed to detecting partial etching in the ferromagnetic pattern of FIG. 10A.

Fast Fourier Transform (FFT) was performed on the time signal obtained at every bias field, and the result plotted as shown in FIG. 12, which plots the square of the frequency of measured time-domain signals as a function of iteration. As can be seen from FIG. 12, three different frequencies are observed. Two of the frequencies (shown by solid lines) increase linearly with magnetic field, while a third frequency (shown by a dashed line) appears to decrease with magnetic field. The third frequency can be ascribed to a nonlinear mixing of the two other frequencies. Close to the value of field where the field changes from an increasing to a decreasing field (i.e. iteration numbers 250, 750, and 1250), the time-domain (and also the frequency-domain) signals are not clear, because these are the values used for background subtraction. Note that all subsequent iteration numbers will correspond to bias magnetic field shown in FIG. 10B.

Representative Aspects of Detecting Defects in Ferromagnetic Films

Defects were etched into thin ferromagnetic films for evaluating, determining, or finding the effect(s) of defects present in the films on spinwave-based measurements performed in accordance with an embodiment of the present disclosure, such as measurements performed by way of procedures described above.

Figures 13A, 13B, 13C:
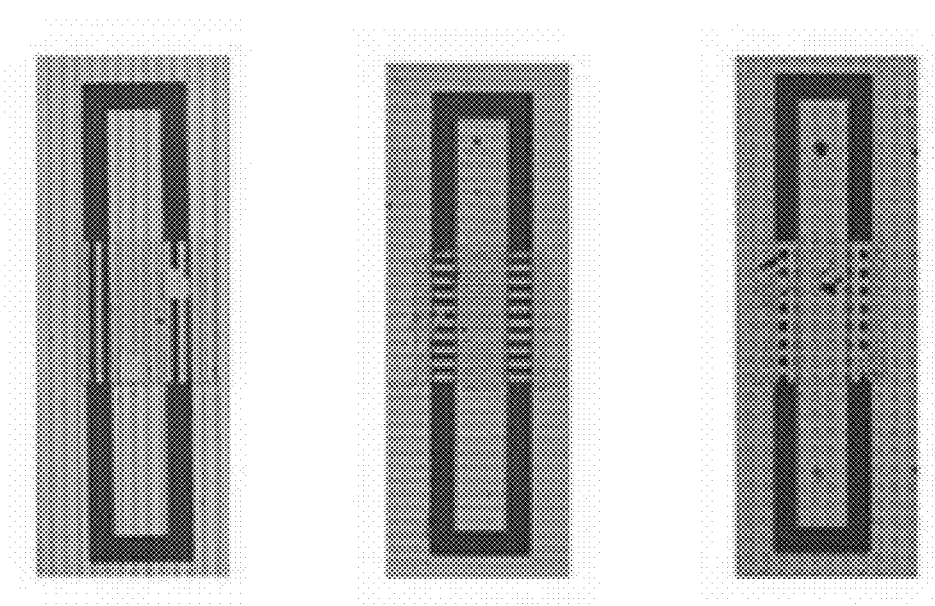
FIGS. 13A-C depict representative types of fabricated ferromagnetic structures and corresponding vertical line defects, horizontal line defects, and circular antidot array defects studied by way of spinwave-based metrology in accordance with an embodiment of the present disclosure.

FIGS. 13A-C depict representative types of ferromagnetic structures or patterns and corresponding or associated defects that were studied for purpose of detecting defects by way of spinwave-based metrology. The ferromagnetic films were rectangular or square permalloy patterns that included particular types of defect structures, which were formed by etching. More particularly, the defects depicted in FIGS. 13A, 13B, and 13C are respectively referred to as 'vertical line defects', 'horizontal line defects,' and 'circular antidot array defects.' Such types of defects are understood by those of ordinary skill in the relevant art.

Vertical Line Defects

Figure 14:
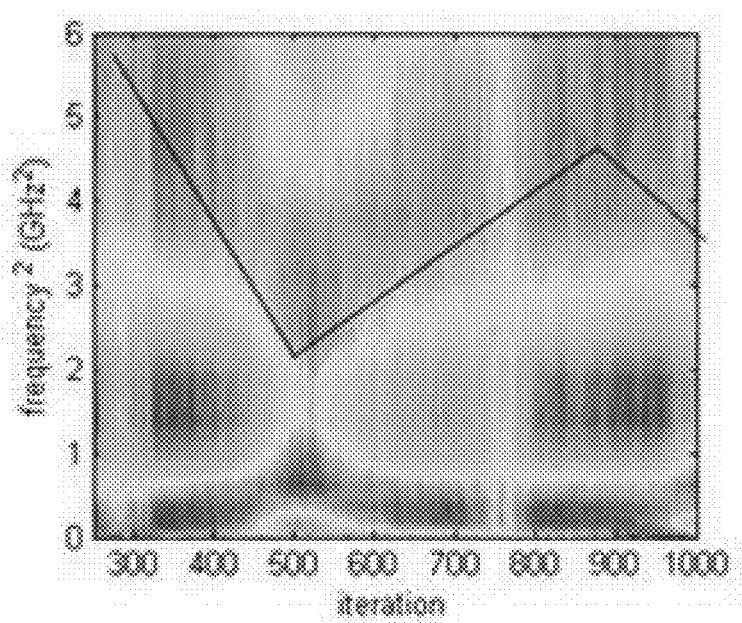
FIG. 14 depicts the frequency spectrum of spinwave measurements corresponding to spinwave measurements performed in accordance with an embodiment of the present disclosure upon a ferromagnetic sample of FIG. 13A having vertical line defects.

FIG. 14 depicts the frequency spectrum of spinwave measurements corresponding to spinwave measurements performed in accordance with an embodiment of the present disclosure upon the ferromagnetic sample of FIG. 13A having vertical line defects. Similar to the previously described measurements, the frequency spectrum shown in FIG. 14 is linear with respect to magnetic field. There is also a low-frequency component that decreases with applied bias magnetic field. In a manner analogous the previous measurement, two rather than three frequency components are visible, indicating that the sample has been etched through its entire thickness. Thus, aspects of the frequency spectrum corresponding to spinwave measurements performed in accordance with embodiments of the present disclosure can be defined as indicators corresponding to the presence of vertical line defects. There is also evidence of asymmetry in this measurement, which can be due to the fact that the vertical lines are not exactly aligned to the waveguide. Hence, spinwave-based metrology can also provide a manner of indicating alignment errors or extracting or estimating (mis)alignment information corresponding to one or more layers of a sample under consideration.

Horizontal Line Defects

Figure 15A:
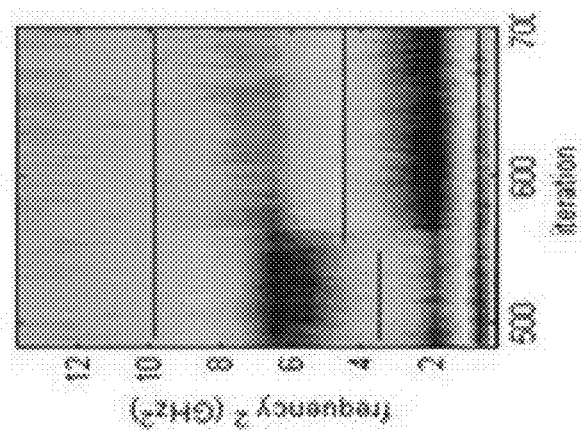
FIGS. 15A-C plot portions the frequency spectrum of spinwave measurements made in accordance with an embodiment of the present disclosure on a NiFe sample of FIG. 13B having horizontal line defects.
Figure 15B:
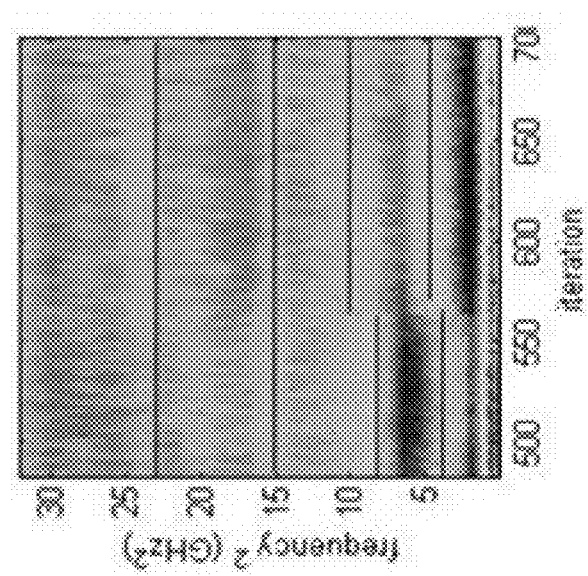
Figure 15C:
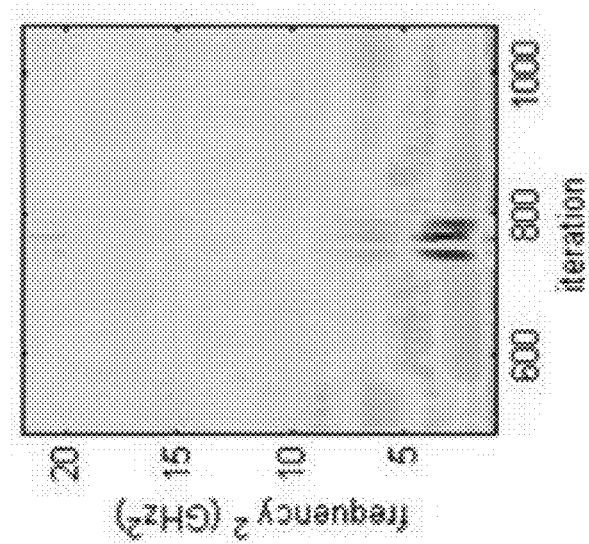

FIGS. 15A-C plot portions the frequency spectrum of spinwave measurements made on a NiFe sample having horizontal line defects. The permalloy structures having horizontal line defects behaved fundamentally differently than those having vertical line defects. With horizontal line defects, some form of frequency quantization is evident, as can be seen in FIGS. 15A-C. As can be seen from FIG. 15A, the frequency characteristics are symmetric between iteration number 500 and 1000. However, upon closer inspection of such frequency characteristics, as shown in FIG. 15B-C, quantization of frequencies is clearly visible. Furthermore, a number of distinct frequency components are observed, which are substantially independent of applied bias magnetic field. Such frequency quantization can be defined as evidence or a characteristic of samples having horizontal line defects.

Circular Antidot Array Defects

Figure 16B:
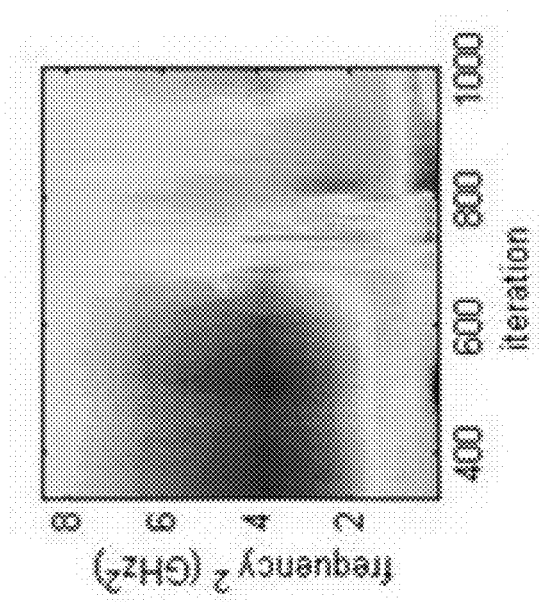
FIGS. 16A-B plot measured frequency characteristics of a permalloy thin film sample of FIG. 13C having circular antidot array defects.
Figure 16A:
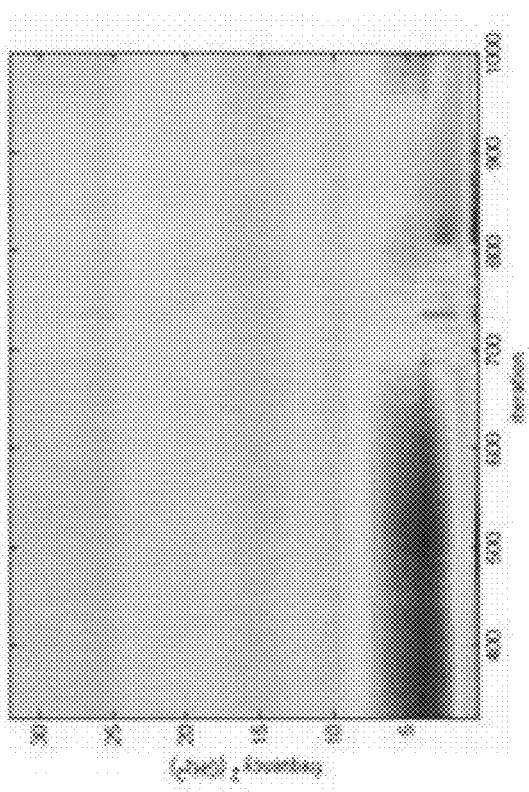

FIGS. 16A-B plot measured frequency characteristics of a permalloy thin film sample having circular antidot array defects. The frequency characteristics of this sample are significantly different from samples that have either horizontal line or vertical line defects. More particularly, a single frequency is observed, which is independent of applied bias magnetic field (i.e., no visible field-dependent characteristics are apparent in the frequency spectrum). Such a frequency spectrum characteristic can thus be defined as an indicator of the presence of circular antidot array defects, which is different or distinct from frequency spectrum indicators corresponding to horizontal line defects or vertical line defects Aspects of Representative Ferromagnetic Film Material Determination Technique As can be seen from FIG. 6B, the spinwave signal decays as a function of time, as the amplitude of the precessions of individual magnetic moments attenuate due to damping. This damping is an entirely material-dependent phenomenon, and can thus be used for evaluating, classifying, characterizing, analyzing, or identifying the material or material composition from whence it emanates.

The impulse-response of FMR signals in the representative spinwave-based metrology apparatus shown in FIG. 5 is driven by the following equation:

$$v(t) = \exp\left(\frac{t-t_0}{\tau}\right)\sin(2\pi f_p t - \phi) \qquad (4)$$

where the sinusoidal component results from the projection of the two-dimensional circular precession of the electronic moments onto the one-dimensional waveguide structure. The precessional frequency $f_p$ shown in Equation (3) has already been discussed above in relation to the determination of the thickness of the sample. Here, the damping parameter ($\lambda$) is of interest, which is related to the decay time constant ($\tau$). The damping parameter can be used to determine the ferromagnetic material or material composition from which the thin film is made. The damping parameter is purely a material property, and can be used to evaluate, classify, characterize, analyze, or identify the material or material composition of a thin film.

The damping parameter is given by the following equation:

$$\lambda = 2/\tau. \qquad (5)$$

One or more portions of a spinwave measurement procedure for evaluating, classifying, characterizing, analyzing, or identifying thin film material composition can be identical, substantially identical, or analogous to the spinwave measurement procedure for determining film thickness. Generally, one measurement is sufficient for determining both the thickness as well as the material composition of a ferromagnetic thin film. Spinwave signals extracted from the previous measurements (such as shown in FIG. 6B) can be used for determining material composition or material type.

Results

Figure 17B:
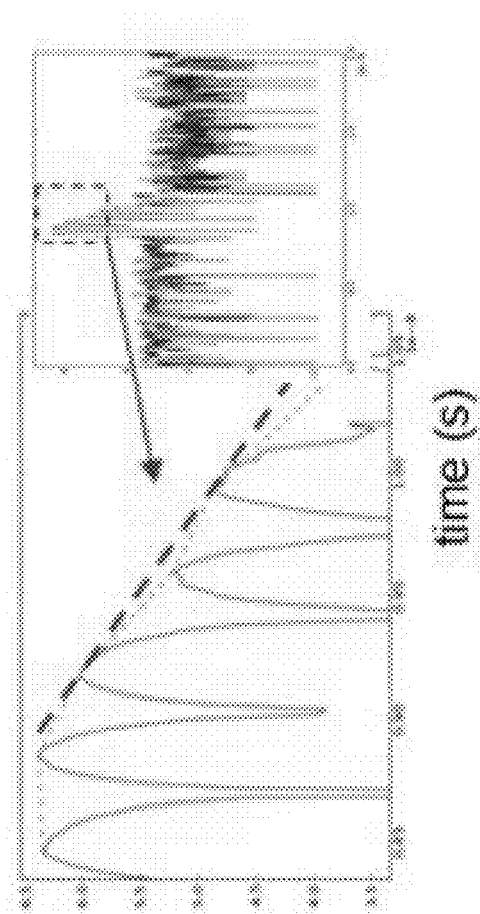
FIGS. 17A-B illustrate portions of a representative procedure or process for detecting exponential spinwave decay behavior.
Figure 17A:
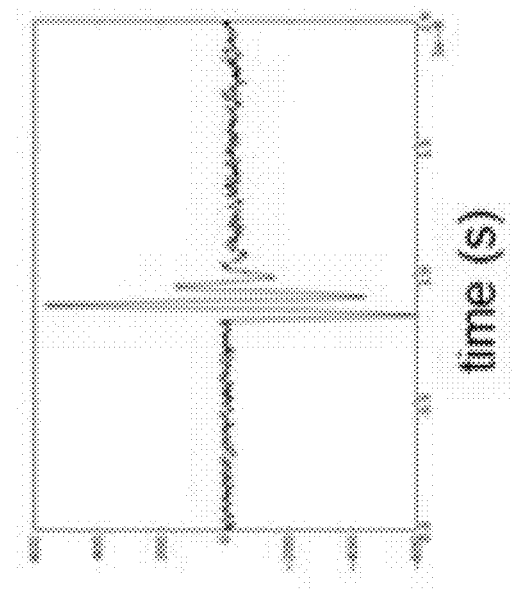

FIGS. 17A-B illustrate portions of a representative procedure or process for detecting the above-referenced exponential decay. More particularly, FIG. 17A depicts a representative (e.g., measured) spinwave FMR signal. The natural logarithm of the magnitude of the representative spinwave FMR signal is plotted in the inset in FIG. 17B. Peak detection is used for finding the magnitude of subsequent peaks, and their time dependences, in a manner indicated shown in FIG. 17B, which illustrates exponential FMR pulse decay. From this data, the slope of exponential decay can be estimated. This is indicated by way of the dotted line in FIG. 17B. From Equation (4), the slope is equal to the inverse of the damping constant ($1/\tau$). Thus, the damping parameter can be calculated using Equation (4).

Figure 18:
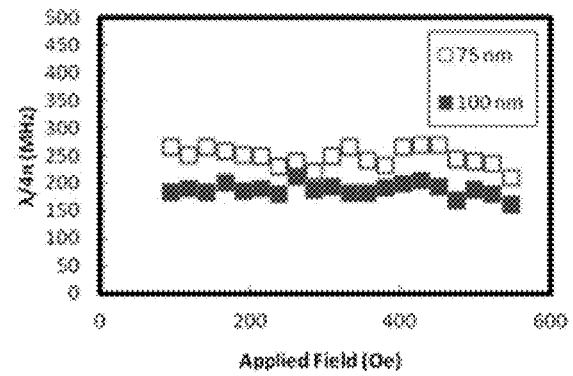
FIG. 18 is a graph indicating measured or estimated damping parameter values for particular ferromagnetic samples under consideration relative to applied bias magnetic field.

FIG. 18 is a graph indicating measured or estimated damping parameter values for particular ferromagnetic samples under consideration relative to applied bias magnetic field. For instance, the calculated damping parameter for a NiFe sample having a thickness of 100 nm is approximately 200 MHz, which is consistent with reported values measured by other means.

Figure 19:
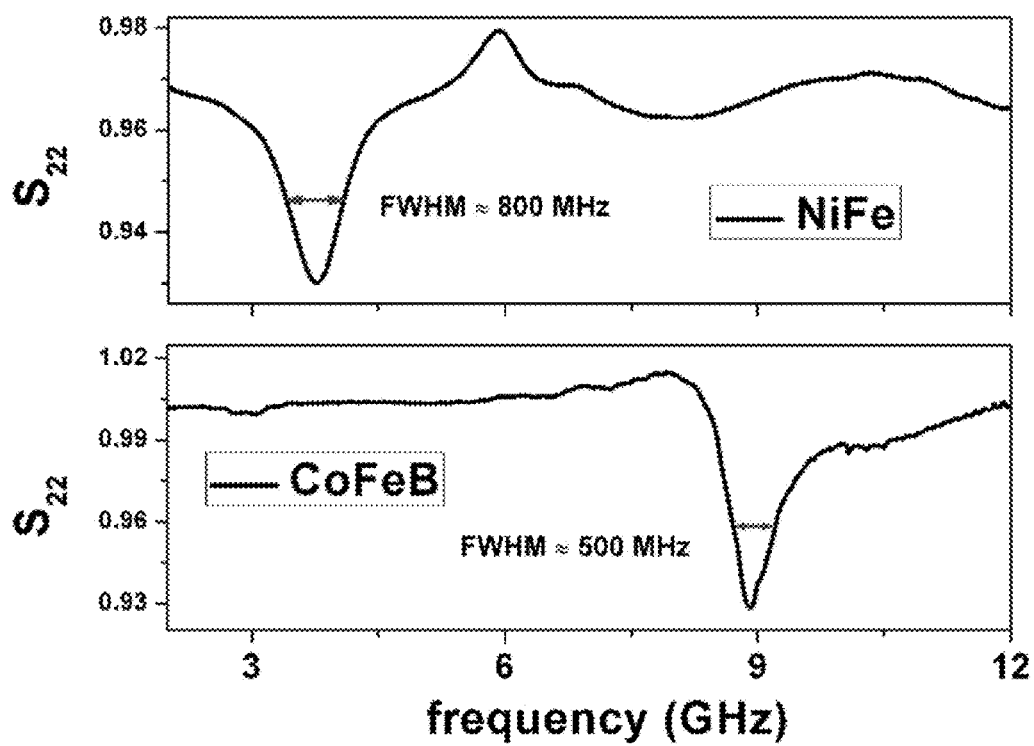
FIG. 19 shows a VNA frequency sweep for a first sample having a CoFeB layer and a second sample having a NiFe layer.

Another way of measuring the damping parameter is by way of a vector network analyzer (VNA). FIG. 19 shows a VNA frequency sweep for a first sample having a CoFeB layer and a second sample having a NiFe layer. At characteristic frequencies, microwave power is absorbed by the ferromagnetic layer, which results in a drop in the signal intensity. The drop resembles or corresponds to a Lorentzian function, with a full-width half max (FWHM) value $\Delta\omega$. The damping constant $\alpha$ is given approximately by the following equation:

$$\alpha = \frac{\Delta\omega}{\gamma\mu M_s}. \qquad (6)$$

From these measurements, different values of $\alpha$ are obtained for CoFeB (0.015) and NiFe (0.018). Using the value of a or a different resonance frequency, different materials or material compositions can be identified.

In view of the foregoing, calculation of one or more damping parameters can facilitate or effectuate the evaluation, classification, characterization, analysis, or identification of a material or material composition of one or more ferromagnetic materials or structures under consideration. Some embodiments in accordance with the present disclosure can use a calculated damping parameter to access or reference a table or database that defines or stores relationships between damping parameter values and material characteristic, property, type, and/or composition information. For instance, in such an embodiment, a material composition measurement process can generate a set of calculated damping parameter values, and use one or more of such values (e.g., a single or an average calculated damping parameter value) to look up or access a material composition identifier. The material composition identifier can further be stored in association with spinwave measurement results under consideration and/or presented or output on a display device.

Aspects of Representative Spinwave-Based Metrology Systems

Spinwave-based metrology or measurement systems, apparatuses, and circuits in accordance with embodiments of the present disclosure can exhibit a wide variety of configurations, for instance, depending upon one or more of embodiment details, expected sample characteristics (e.g., material, structure, device, or feature geometry, area, or dimension), desired spatial resolution corresponding to spinwave measurements to be performed upon areas to be tested, and manufacturing or test environment throughput objectives, demands, or requirements. Furthermore, a spinwave-based measurement process or procedure in accordance with the present disclosure can involve one or more manners of applying or delivering microwave radiation to a sample under consideration; and one or manners of detecting aspects of spinwave behavior in the sample. Correspondingly, a spinwave-based metrology system or apparatus can include one or more appropriate types of circuits or circuit elements configured for providing microwave radiation and detecting a spinwave-related response thereto. Aspects of particular representative, yet non-limiting, spinwave-based metrology systems, apparatuses, and circuits are described in detail hereafter to further aid understanding.

Aspects of Representative Spinwave-Based Testing System/Apparatus Configurations FIGS. 20A-D are schematic illustrations showing portions of a spinwave-based metrology or measurement system, apparatus, or device 100 in accordance with an embodiment of the present disclosure. In an embodiment, the apparatus 100 includes a measurement unit 110 respectively coupled to each of a generator unit 150 and a detector unit 160 by way of a first set of microwave lines 140a and a second set of microwave lines 140b; a bias magnetic field unit 170; and a stage or stage assembly 190.

The bias magnetic field unit 170 is configured for applying a set of bias magnetic fields to the DUT 190, and the measurement unit 110 is configured for applying or delivering microwave radiation to portions of the DUT 190 when the bias magnetic field unit 170 is applying a bias magnetic field to the DUT 190, thereby facilitating spinwave-based measurements in manners identical, analogous, or generally analogous to that described above. The measurement unit 110 is further configured for detecting or generating one or more types of response signals that correspond to the behavior of spinwaves in the DUT 190. For instance, in a number of embodiments, the measurement unit 110 is configured for generating by way of magnetic induction response voltage signals corresponding to the behavior of spinwaves in the DUT 190.

Figure 20D:
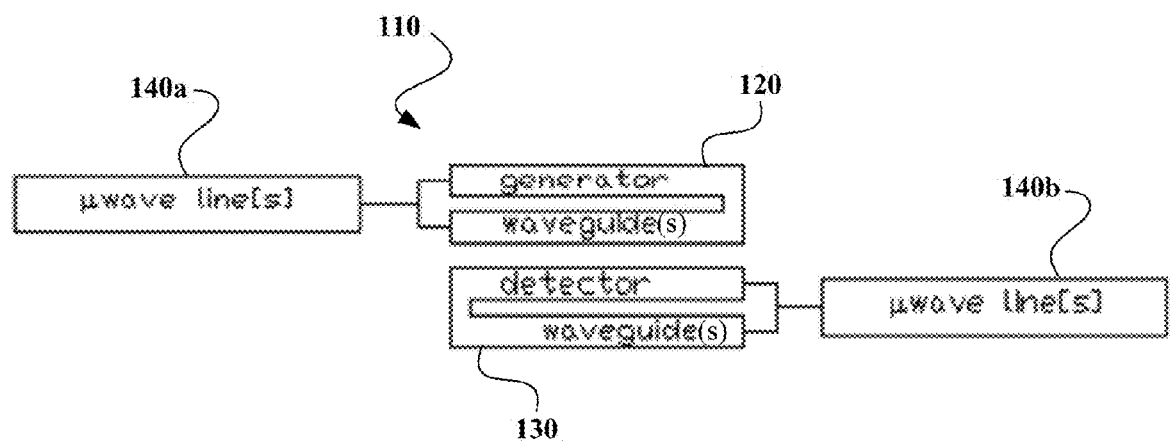

FIG. 20B is a side view showing a measurement unit 110, FIG. 20C is a first top view showing the measurement unit 110, and FIG. 20D is a second top view showing a measurement unit 110 in accordance with an embodiment of the present disclosure. The number, type(s), and organization of material and/or circuit structures or elements within the measurement unit 110 can depend upon embodiment details. In general, the measurement unit 110 includes a set of waveguides or waveguide elements or structures, such as a set of generator waveguides 120 coupled to the first set of microwave lines 140a, and a set of detector waveguides 130 coupled to the second set of microwave lines 140b. The set of generator waveguides 120 and the set of detector waveguides 130 can include patterned or integrated waveguide layers, structures, or elements fabricated in accordance with microscale and/or nanoscale fabrication techniques (e.g., semiconductor or related types of materials, structure, or device manufacturing processes).

In the embodiment shown in FIG. 20D, the measurement unit 110 includes a single generator waveguide or waveguide element or structure 120 coupled to a first microwave line 140a, and a single detector waveguide or waveguide element or structure 130 coupled to a second microwave line 140b. In a representative embodiment for a SiO2 substrate and a NiFe sample, the generator waveguide 120 can have a signal line of approximately 10 μm, a signal—ground width of approximately 5 μm, a ground width of approximately 30 μm, a length of approximately 10 μm, and a waveguide thickness of greater than approximately 200 nm; and the detector waveguide 130 can have identical or essentially identical dimensions. A separation distance between the generator waveguide 120 and the detector waveguide 130 can be approximately 20 μm.

The set of generator waveguides 120 is coupled to the generator unit 150 by way of the first set of microwave lines 140a, and the set of detector waveguides 130 is coupled to the detector unit 160 by way of the second set of microwave lines 140b. The generator unit 150 is configured for supplying or providing microwave frequency electrical signals to the set of generator waveguides 120, and can include, for instance, a function generator, in a manner readily understood by one of ordinary skill in the relevant art. The detector unit 160 is configured for detecting, measuring, processing, and/or analyzing microwave frequency electrical signals carried by the set of detector waveguides 130, and can include, for instance, one or more of a spectrum analyzer, a real-time oscilloscope, a sampling oscilloscope, a vector analyzer, or another type of signal detection or capture device, in a manner also readily understood by one of ordinary skill in the relevant art.

During spinwave measurement procedures, one or more intended or appropriate portions of the DUT 190 are positioned between the measurement unit 110 and the bias magnetic field unit 170 such that spinwaves can be generated or excited in such portions of the DUT 190, and the behavior of such spinwaves in the DUT can be detected. More particularly, the DUT 190 is positioned relative to the bias magnetic field unit 170 such that a bias magnetic field provided by the bias magnetic field unit 170 can establish corresponding electron precession in the portion(s) of the DUT 190 under consideration; and the DUT 190 is positioned relative to the measurement unit 110 such that materials, structures, features, or devices of interest carried by or disposed on/within the portion(s) of the DUT 190 under consideration can be exposed to the microwave radiation produced by the set of generator waveguides 120.

The bias magnetic field unit 170 can include one or more types of magnetic field sources or generators configured for producing magnetic fields appropriate for spinwave-based measurements in accordance with embodiments of the present disclosure. For instance, in some embodiments the bias magnetic field unit 170 includes one or more electromagnets, permanent magnets, and/or projection type electromagnets. A representative range of magnetic field magnitudes providable by the bias magnetic field unit 170 can be approximately 100 Oe for a NiFe sample, and approximately 1 T for a CoFe sample. Depending upon embodiment details, the bias magnetic field unit 170 and the DUT 190 can be positioned or positionable relative to each other such that bias magnetic fields can be provided, applied, or delivered above or below the DUT 190 (e.g., transverse to a plane corresponding to a surface or layer of the DUT 190) and/or beside the DUT 190 (e.g., within or parallel to a plane corresponding to a surface or layer of the DUT 190). For instance, the bias magnetic field unit 170 and the DUT 190 can be relatively positioned or positionable such that (a) forward volume waves can be applied or delivered transverse or substantially transverse to a planar or generally planar layer or surface of the DUT 190; and/or (b) surface or backward volume waves can be applied or delivered parallel or substantially parallel to a planar or generally planar layer or surface of the DUT 190.

With respect to the set of generator waveguides 120, when the generator unit 150 outputs microwave frequency electrical signals, the propagation of such signals along the set of generator waveguides 120 results in the generation of microwave radiation in the spatial region surrounding the set of generator waveguides 120. This microwave radiation will exist in accordance with a spatial radiation distribution or radiation pattern that depends upon the physical design of the set of generator waveguides 120 and the parameters of the microwave electrical signals carried thereby, in a manner readily understood by one of ordinary skill in the relevant art. In various embodiments, the DUT 190 is positioned or positionable relative to the set of generator waveguides 120 such that one or more DUT layers, surfaces, or structures under consideration are exposed to the Oersted field generated by the set of generator waveguides 120, in a manner understood by one of ordinary skill in the relevant art. In a representative embodiment, a planar or generally planar exterior/outermost DUT layer or surface is positioned or positionable at a separation distance of approximately 500 nm from the measurement unit 110.

A spinwave generation region can be defined as a spatial volume or region in which bias magnetic fields and microwave radiation can simultaneously be provided to one or more target spinwave measurement regions, locations, or sites of a DUT 190, such that spinwave-based measurements can be performed upon the target DUT spinwave measurement site(s). Depending upon embodiment details, the bias magnetic field unit 170 and the set of generator waveguides 110 are configured for providing at least one, and possibly multiple, spinwave generation regions.

In order for spinwave measurement(s) to occur at or within intended target DUT spinwave measurement site(s), the DUT 190 must be appropriately positioned relative to the bias magnetic field unit 170, the set of generator waveguides 120, and the set of detector waveguides 130. In the embodiment shown in FIG. 20A, a spinwave generation region can be defined adjacent or beneath (e.g., substantially directly beneath) a lower plane of the measurement unit 110, above an upper plane of the stage assembly 180, and within a spatial area defined by the geometry or bounds of the measurement unit's set of generator waveguides 120.

Figure 21A:
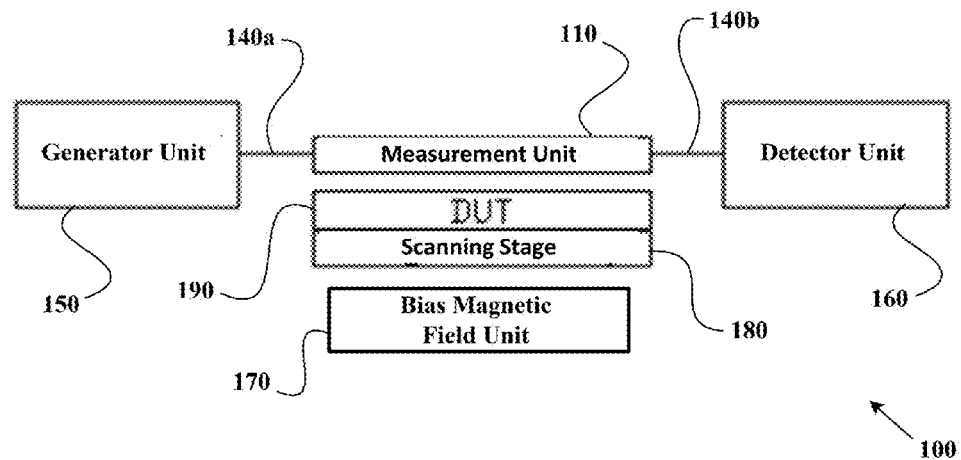
FIG. 21A is a schematic illustration showing portions of a spinwave-based measurement apparatus in which the stage assembly is configured for carrying and displacing a DUT while a measurement unit and a bias magnetic field unit remain fixed relative to the stage assembly.
Figure 21B:
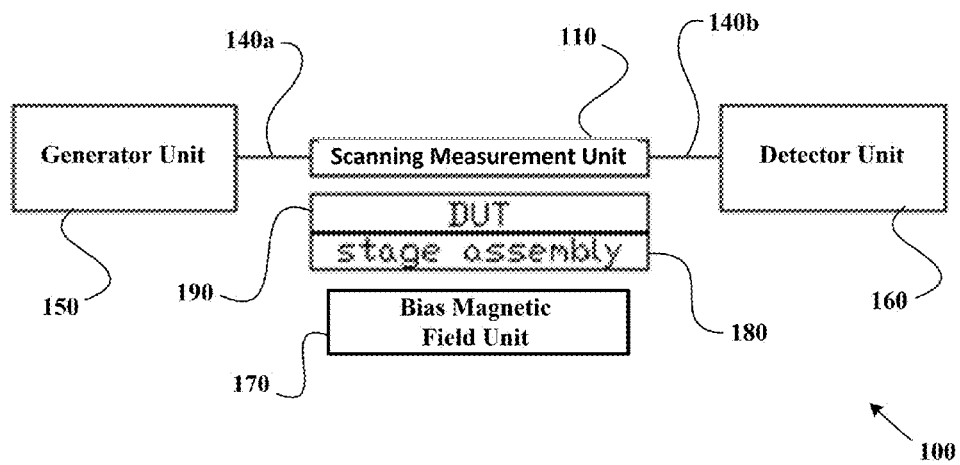
FIG. 21B is a schematic illustration showing portions of a spinwave-based measurement apparatus in which a measurement unit and a bias magnetic field unit are configured for displacement while a stage assembly maintains a DUT in a stationary position.

The stage assembly 180 can carry or support one or more portions of the DUT 190. In various embodiments, the stage assembly 180 is displaceable, and is configured for moving portions of the apparatus 100 and/or the DUT 190 in a controlled or controllable (e.g., programmable/selectable) manner to facilitate spinwave measurements at, within, and/or across a set of intended target DUT spinwave measurement sites. FIG. 21A is a schematic illustration showing portions of a spinwave-based measurement apparatus 100 in which the stage assembly 180 is configured for carrying and displacing the DUT 190, while the measurement unit 110 and the bias magnetic field unit 170 remain fixed relative to the stage assembly 180. Alternatively, FIG. 21B is a schematic illustration showing portions of a spinwave-based measurement apparatus 100 in which the measurement unit 110 is configured for displacement while the stage assembly 180 maintains the DUT 190 in a stationary position. Depending upon embodiment details, the bias magnetic field unit 170 can be stationary/fixed or displaceable.

Figure 22A:
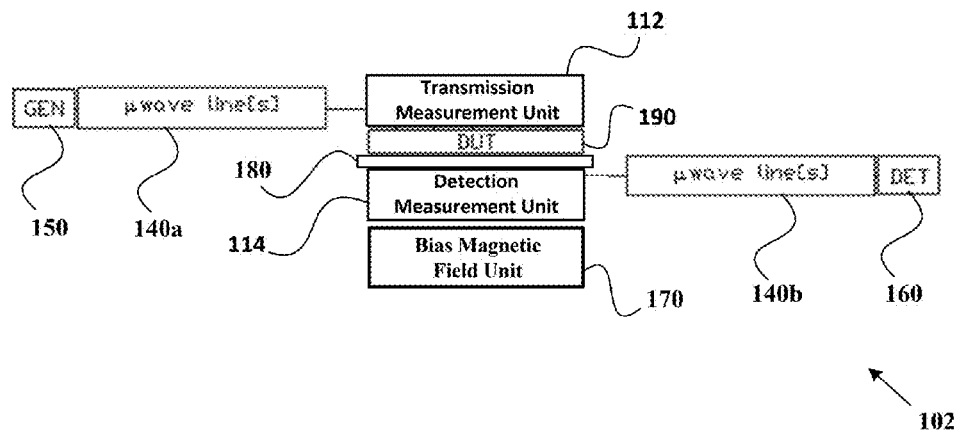
FIGS. 22A-22B are schematic illustrations showing portions of a spinwave-based metrology or measurement apparatus or device configured for transmission spinwave metrology or measurements in accordance with an embodiment of the present disclosure.
Figure 22B:
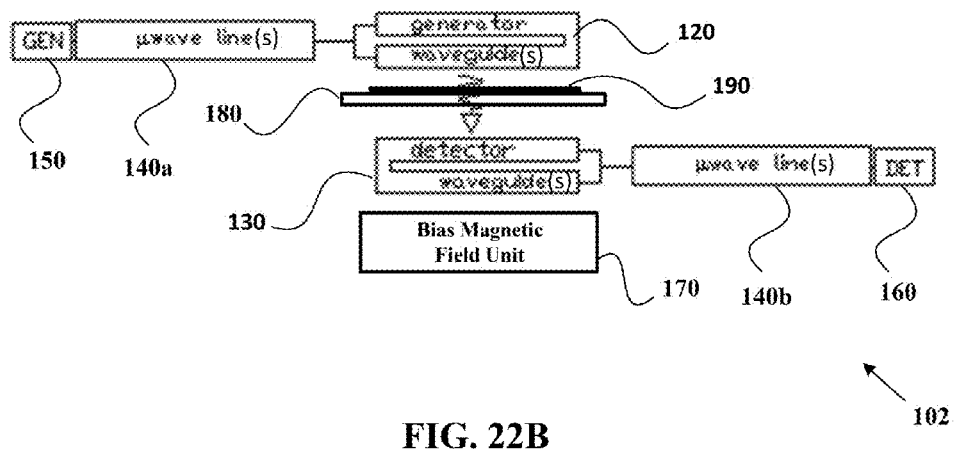

FIGS. 22A-22B are schematic illustrations showing portions of a spinwave-based metrology or measurement apparatus or device 102 configured for transmission spinwave metrology or measurements in accordance with another embodiment of the present disclosure. In an embodiment, the apparatus 102 includes a transmission measurement unit 112 such as a set of generator waveguides or waveguide structures or elements 120 coupled to a generator unit 150 by a first set of microwave lines 140a; and a detection measurement unit 114 such as a set of detector waveguides or waveguide structures or elements 130 coupled to a detector unit 160 by a second set of microwave lines 140b. The apparatus 102 further includes a bias magnetic field unit 170; and a stage or stage apparatus 180. Each such element of the apparatus 102 can have a structure and function that is identical, substantially identical, analogous, or similar to that described above.

The set of generator waveguides 120 and the set of detector waveguides 130 are spatially offset from each other in a direction transverse to a lower plane of the set of generator waveguides 120 and an upper plane of the set of detector waveguides 130. The stage apparatus 180 includes an upper plane configured for carrying or supporting portions of at least one DUT 190, such that the DUT 190 is disposed between the lower plane of the set of generator waveguides 120 and the upper plane of the set of detector waveguides 130. The bias magnetic field unit 170 is configured for providing bias magnetic fields within the spatial region between the lower plane of the set of generator waveguides 120 and the upper plane of the set of detector waveguides 130. Depending upon embodiment details and/ or a spinwave measurement mode under consideration (e.g., corresponding to an intended spinwave mode to be excited), such bias magnetic fields can extend or be directed or oriented (a) transverse; or (b) parallel to a set of planar or generally planar layers or surfaces of the DUT 190 (e.g., including an outermost or exterior DUT layer or surface). Thus, in the embodiment shown in FIG. 22, a spinwave generation region can be defined between the lower plane of the set of generator waveguides 120 and the upper plane of the set of detector waveguides 130, with a cross-sectional area parallel to such planes defined by the geometry or bounds of the set of generator waveguides 120.

Relative positioning between a DUT 190, the set of generator waveguides 120, the set of detector waveguides 130, and the bias magnetic field unit 170 can occur in different manners depending on embodiment details. For instance, the stage assembly 180 can be configured for displacing the DUT 190 while the set of generator waveguides 120, the set of detector waveguides 130, and the bias magnetic field unit 170 remain stationary. Additionally or alternatively, the set of generator waveguides 120, the set of detector waveguides 130, and the bias magnetic field unit 170 can be configured for displacement while the stage assembly 190 maintains the DUT 190 in a stationary position.

The set of generator waveguides 110 can be configured for receiving first, test, or probe electrical signals from the generator unit 150, and generating first, test, or probe microwave radiation corresponding thereto. Such microwave radiation will be generated in accordance with a given or intended spatial radiation distribution or pattern corresponding to the physical design of the set of generator waveguides 120 and the characteristics of the test or probe electrical signals, in a manner readily understood by one of ordinary skill in the relevant art. The probe microwave radiation can travel to and through portions of the DUT 190, and spinwaves therein can interact with, affect, modulate, or perturb the probe radiation thereby resulting in response radiation. Upon exposure to the response radiation, second, received, or response electrical signals are carried by or propagate along the set of detector waveguides 130. Such response electrical signals are provided to the detector unit 160.

Figure 23:
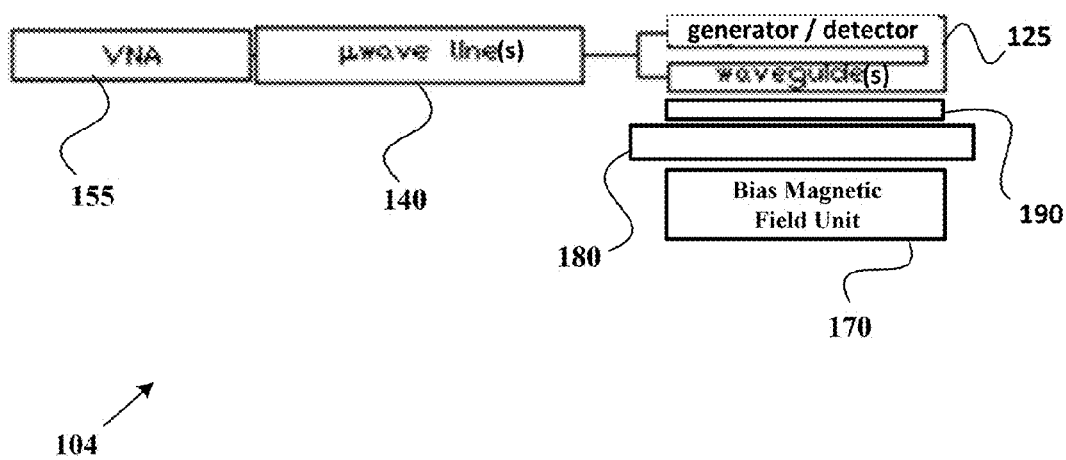
FIG. 23 is a schematic illustration showing portions of a spinwave-based metrology or measurement apparatus or device configured for making reflection spinwave measurements in accordance with an embodiment of the present disclosure.

FIG. 23 is a schematic illustration showing portions of a spinwave-based metrology or measurement apparatus or device 104 configured for making reflection spinwave measurements in accordance with an embodiment of the present disclosure. In an embodiment, the apparatus 104 includes a set of generator/detector waveguides or waveguide structures or elements 125 configured for carrying microwave frequency electrical signals and generate microwave radiation corresponding thereto. Generated microwave radiation exhibits a spatial radiation pattern, in a manner described above. The set of generator/detector waveguides 125 is coupled to a generator/detector unit 155 such as a vector network analyzer (VNA) by way of a set of microwave lines 140. The apparatus 104 additionally includes a bias magnetic field unit 170 configured for providing a set of bias magnetic fields within the spatial extent of the microwave radiation generated by the set of generator/detector waveguides 125; and a stage assembly 180 configured for carrying or supporting portions of a DUT 190.

At least one spinwave generation region can be defined between a lower plane of the set of generator/detector waveguides 125 and an upper plane of the stage assembly 180 in a manner identical or analogous to that described above. One or more target DUT spinwave measurement sites can be positioned or oriented within a spinwave generation region, such that spinwave measurements can be performed upon, at, or within the target DUT spinwave measurement site(s) exposed to each of a bias magnetic field and microwave radiation. The set of generator/detector waveguides 125 outputs microwave radiation to the DUT 190, and receives reflected microwave radiation from the DUT 190. Spinwaves within the DUT 190 can interact with, affect, modulate, or perturb microwave radiation incident upon the DUT 190, and thus the reflected microwave radiation carries, includes, or incorporates information (e.g., absorption spectra characteristics) corresponding to the spinwaves within the DUT 190.

Aspects of Representative Generator/Detector Waveguide Array Configurations

In some embodiments, spinwave measurements can be made by way of multiple generator waveguides 120 and detector waveguides 130 organized or fabricated in array or array type patterns. Such array or array type organizations of generator waveguides 120 and detector waveguides 130 can facilitate spinwave testing of multiple target DUT spinwave measurement sites on a selective (e.g., individual/sequential) or simultaneous basis, relative to one or multiple DUTs 190 depending upon embodiment details.

Figure 24A:
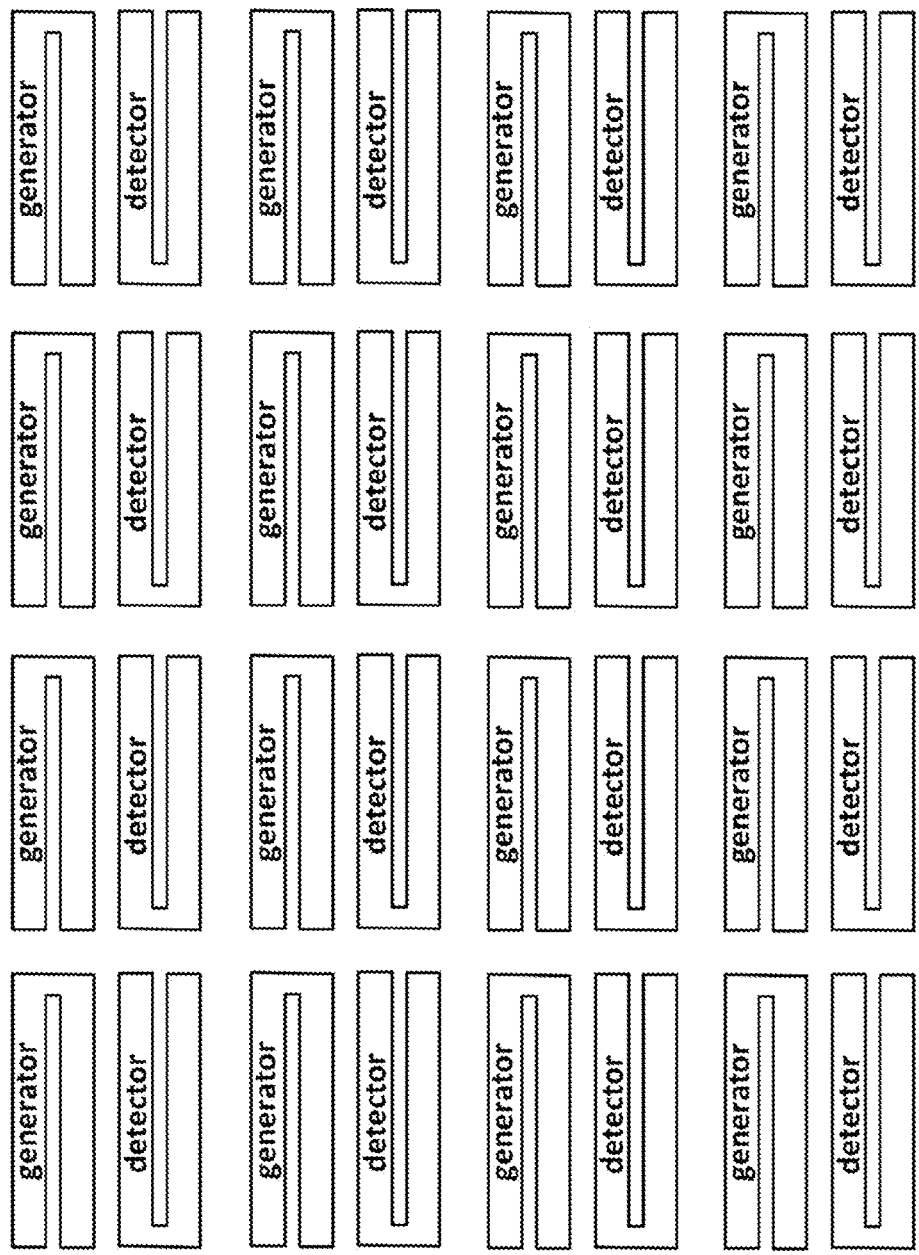
FIGS. 24A-C are schematic illustrations of representative generator/detector waveguide arrays in accordance with embodiments of the present disclosure.
Figure 24B:
Figure 24C:
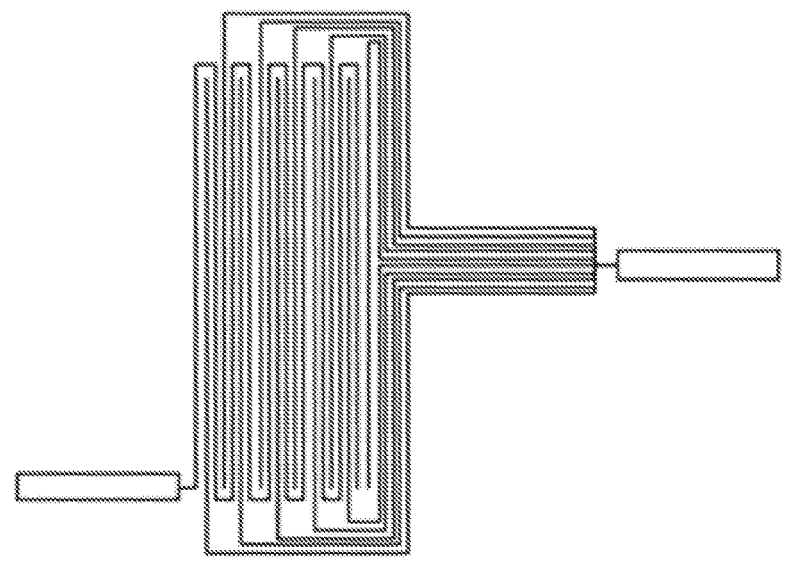
Figure 25:
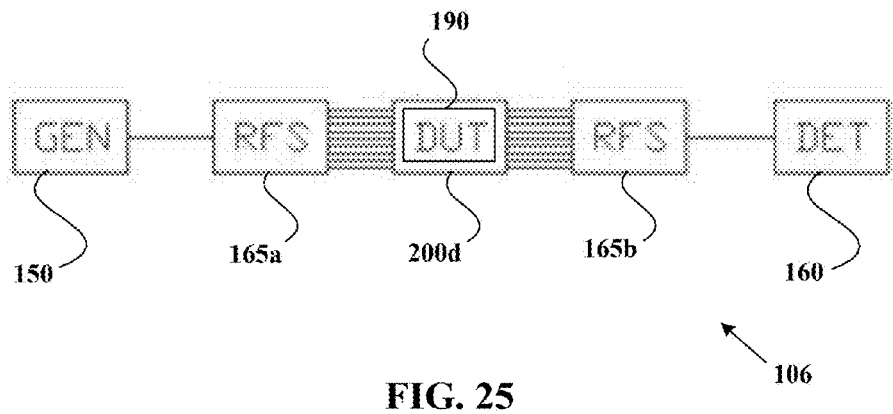
FIG. 25 is a schematic illustration showing portions of a spinwave-based measurement apparatus in which a first microwave frequency switch is disposed between a generator unit and a generator/detector array, and a second microwave frequency switch is disposed between the generator/detector array and a detector unit.
Figure 26:
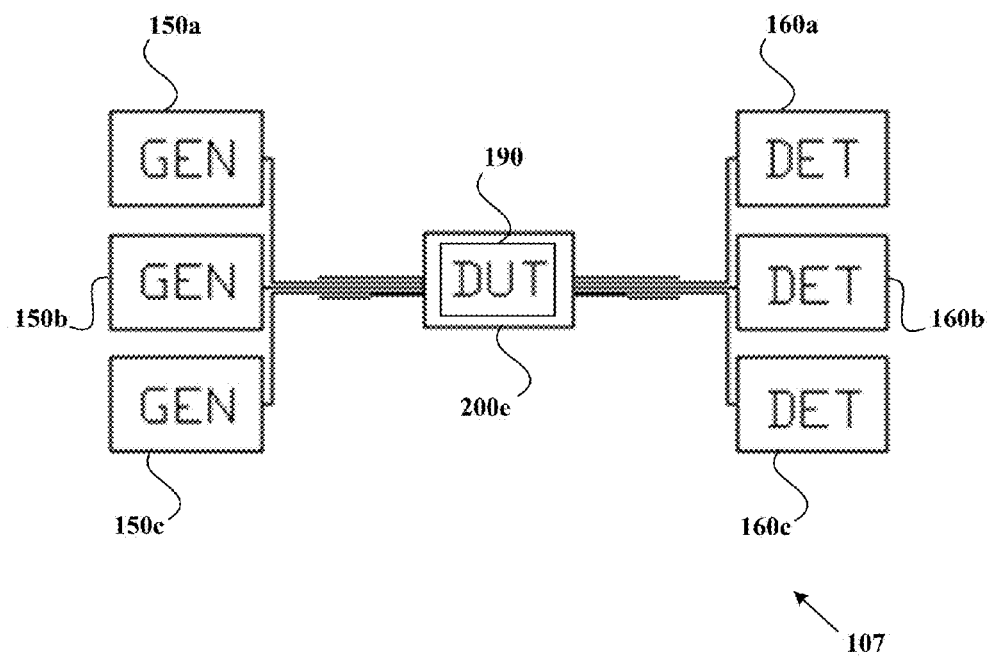
Figure 27:
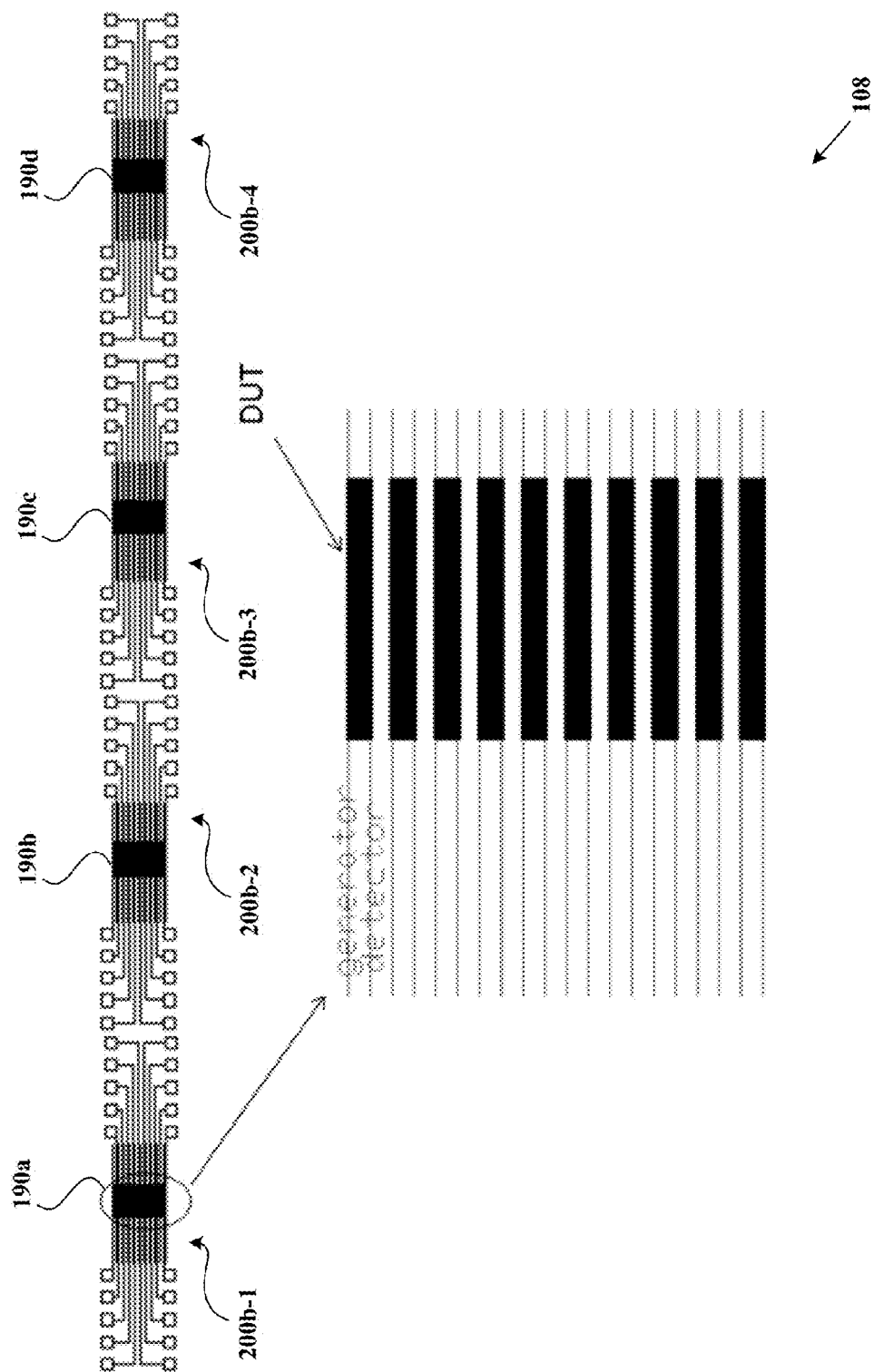
FIG. 27 is a schematic illustration showing portions of a spinwave-based measurement apparatus configured for performing spinwave testing on a 10×4 DUT array by way of 4 generator/detector waveguide arrays, each of which is configured for testing an array of 10 DUTs.

FIGS. 24A-C are schematic illustrations of representative generator/detector waveguide arrays 200a-c in accordance with embodiments of the present disclosure. Embodiments in accordance with the present disclosure which are configured for selectively performing spinwave-based measurements using individual generator/detector waveguide pairs within a generator/detector waveguide array can include appropriate type(s) of switching or signal path selection elements. For instance, FIG. 25 is a schematic illustration showing portions of a spinwave-based measurement apparatus 106 in which a first microwave frequency switch 165a is disposed between a generator unit 150 and a generator/detector array 200d, and a second microwave frequency switch 165b is disposed between the generator/detector array 200d and a detector unit 160. Embodiments in accordance with the present disclosure which are configured for performing simultaneous spinwave-based measurements can include multiple generator units 150 and multiple detector units 160, in a manner schematically illustrated in a representative embodiment 107 shown in FIG. 26. To further aid understanding in view of the foregoing, FIG. 27 is a schematic illustration showing portions of a spinwave-based measurement apparatus 108 configured for performing spinwave testing on a 10×4 DUT array including a first through a fourth DUT 190a, 190b, 190c, 190d by way of 4 generator/detector waveguide arrays 200b-1, 200b-2, 200b-3, 200b-4, each of which is configured for testing an array of 10 DUTs 190.

Further Aspects of Representative Detector Units

A detector unit 160 or a generator/detector unit 155 is configured for processing and/or analyzing received electrical signals. A detector unit 160 or a generator/detector unit 155 can further be configured for generating corresponding spinwave-based measurement information, data, or results, such as one or more types of spinwave-based measurement information or results described herein (e.g., material thickness information, indicators, data, or values; material integrity or irregularity information, indicators, or data; manufacturing defect information, indicators, or data; and/or material composition or type information, indicators, identifiers, or data). In several embodiments, a detector unit 160 or a generator/detector unit 155 includes or is coupled to one or more types of processing or computing resources, such as a computing device or computer system having one or more processing units, memory (e.g., random access memory (RAM) and read-only memory (ROM)), data storage (e.g., one or more magnetic and/or optical disk drives), user interface devices (e.g., a mouse or other type of pointing device(s), a keyboard, and a display device). The detector unit 160 or generator/detector unit 155 can further include communication resources (e.g., a network interface card) by which the detector unit 160 or generator/detector unit 155 can be coupled to a network such as the Internet and/or a Local Area Network (LAN).

A computing device or computing system to which a detector unit 160 or a generator/detector unit 155 is coupled can include one or more types of computer readable media (e.g., one or more types of fixed and/or removable memory or data storage media) for storing program instructions that, when executed, manage or control the performance spinwave-based testing procedures and/or the generation of spinwave-based measurement information or results in accordance with embodiments of the present disclosure.

Aspects of Representative Spinwave-Based Metrology/Inspection Processes

Figure 28:
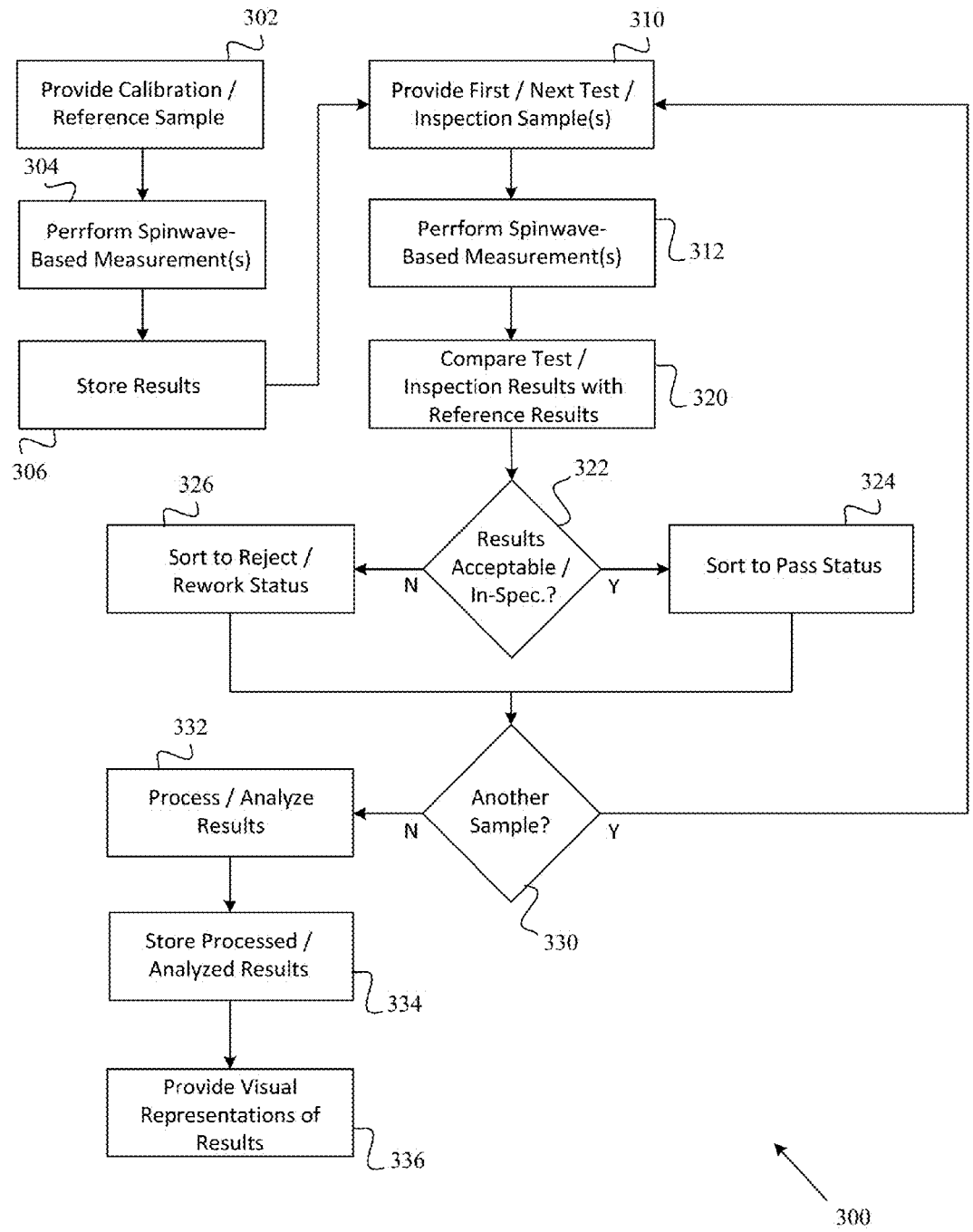
FIG. 28 is a flow diagram of a representative spinwave-based inspection/measurement process in accordance with an embodiment of the present disclosure.

FIG. 28 is a flow diagram of a representative spinwave-based inspection and/or measurement process 300 in accordance with an embodiment of the present disclosure. In an embodiment, the process 300 includes a first process portion 302 involving providing a set of calibration or reference samples, and second and third process portions 304, 306 involving performing a set of spinwave-based and/or other types of measurements on the reference sample(s) and storing corresponding calibration or reference results. A calibration or reference sample can include a sample having known (e.g., predetermined or a-priori known) characteristics or properties, or a sample having characteristics or properties that are expected to fall within particular (e.g., expected good or expected in-specification) ranges (e.g., a sample from a production line that was recently or very recently qualified as in-specification).

A fourth process portion 310 involves providing a first or next test or inspection sample, and a fifth process portion 312 involves performing a set of spinwave-based measurements on the current test sample, for instance, one or more noninvasive measurements of a type described herein. Sixth through ninth process portions 320-326 involve comparing spinwave-based measurement results obtained for the current test sample with calibration or reference sample results; determining whether the current results are in-specification or out-of-specification; and sorting, marking, or otherwise identifying the current inspection sample in accordance with a pass status or a fail/reject/rework status based upon the comparison.

If another test or inspection sample requires consideration, a tenth process portion 330 can return control to the fourth process portion 310. Otherwise, in an embodiment an eleventh process portion 332 involves processing or analyzing spinwave-based measurement results across one or more test or inspection samples. The eleventh process portion 332 can involve, for instance, statistical analysis of spinwave-based measurement results. Such analysis can be directed to identifying variations in or distributions of one or more spinwave-based measurement values across a set of samples (e.g., thereby identifying material, structural, or device-related processing variations); characterizing or categorizing spinwave-based measurement results in accordance with one or more relationships, mappings, or correlations between the spinwave-based measurement results and types of manufacturing errors or defects (e.g., different categorical types of defects described above). A twelfth process portion 334 involves storing such processing/analysis results, and a thirteenth process portion 336 involves providing visual representations of such analysis results (e.g., providing electronic or hardcopy versions of sample or wafer maps that indicate occurrence or distribution of manufacturing process variations or errors correlated with or determined by way of spinwave-based measurements).

Figure 29A:
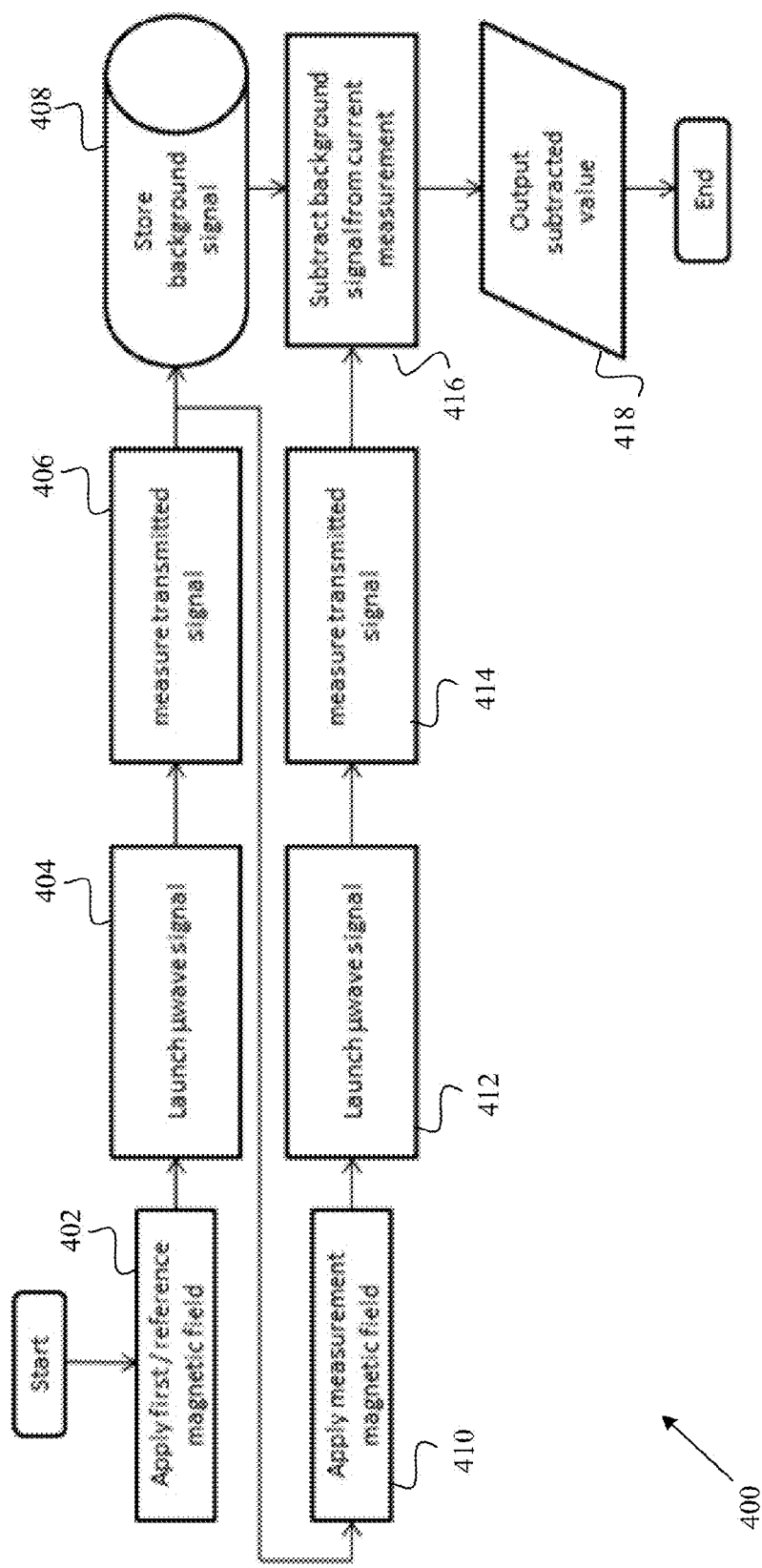
FIG. 29A is a flow diagram of a process for performing transmission spinwave-based measurements in accordance with an embodiment of the present disclosure.

FIG. 29A is a flow diagram of a process 400 for performing transmission spinwave-based measurements in accordance with an embodiment of the present disclosure. In an embodiment, the process 400 includes a first process portion 402 involving providing or applying a first, reference, or background bias magnetic field; a second process portion 404 involving launching a microwave signal (e.g., using a set of waveguides, in a manner described herein); and a third process portion 406 involving measuring (e.g., by way of a set of waveguides configured for receiving the launched microwave signal) one or more properties (e.g., power, amplitude, etc. . . . ) of a transmitted microwave signal. A fourth process portion 408 involves storing such properties as a definition of a background signal.

A fifth process portion 410 involves providing or applying a measurement bias magnetic field. A sixth process portion 412 involves launching a microwave signal, and a seventh process portion 414 involves measuring a transmitted signal corresponding to the launched microwave signal. An eighth process portion 416 involves subtracting the background signal from the current measured transmitted signal, and a ninth process portion 418 involves storing, communicating, or outputting corresponding subtracted signal data or a set of subtracted signal values.

Figure 29B:
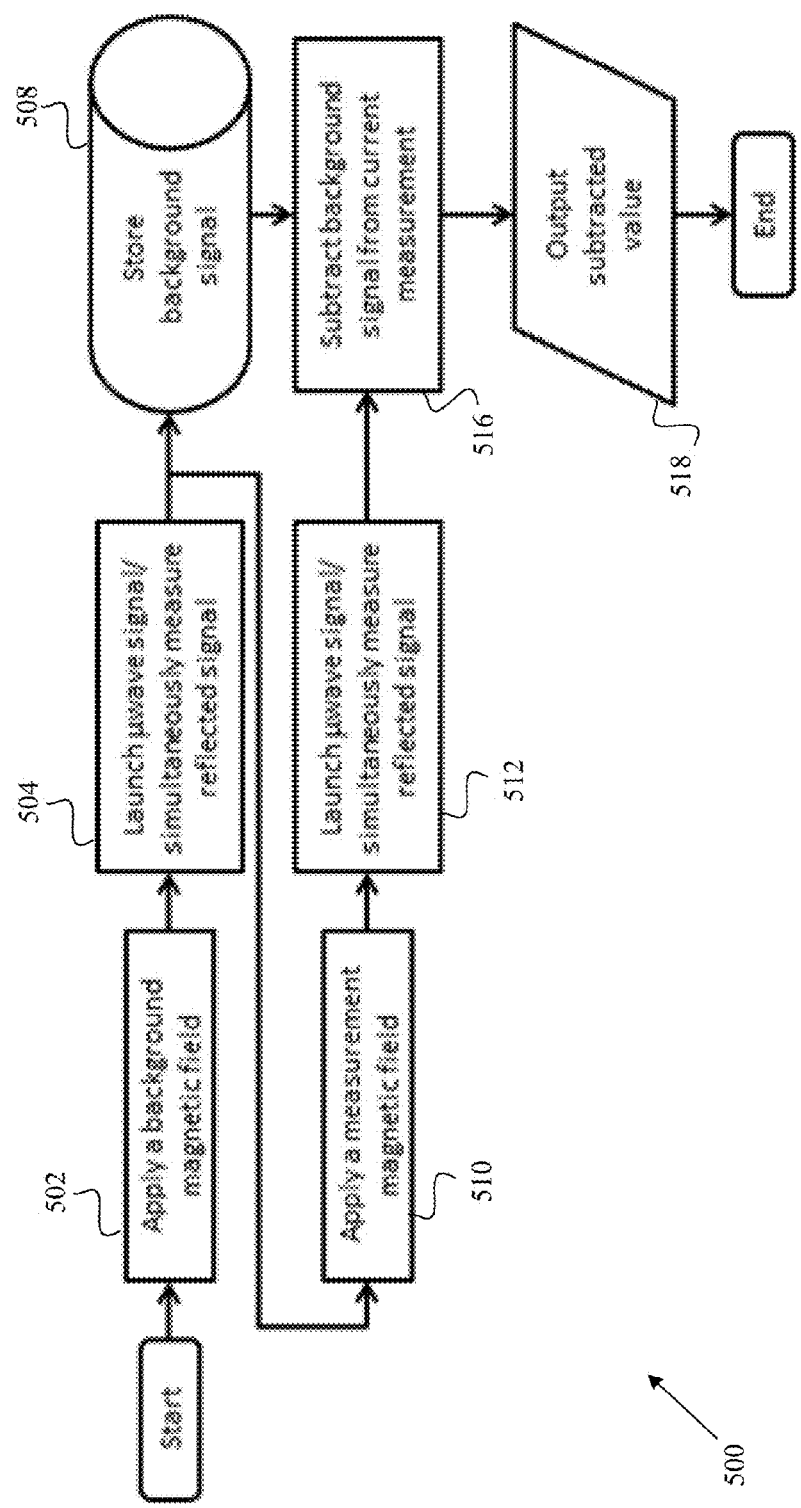
FIG. 29B is a flow diagram of a process for performing reflection spinwave-based measurements in accordance with an embodiment of the present disclosure.

FIG. 29B is a flow diagram of a process 500 for performing reflection spinwave-based measurements in accordance with an embodiment of the present disclosure. In an embodiment, the process 500 includes a first process portion 502 involving providing or applying a background bias magnetic field, and a second process portion 504 involving launching a microwave signal and simultaneously measuring a reflected signal. A third process portion 508 involves storing the measured reflected signal as a background signal.

A fourth process portion 510 involves providing or applying a measurement bias magnetic field, and a fifth process portion 512 involves launching a microwave signal and simultaneously measuring a reflected signal. A sixth process portion 516 involves subtracting the background signal from the current measured reflected signal, and a seventh process portion 518 involves storing, communicating, or outputting corresponding subtracted signal data or a set of subtracted signal values.

Figure 30:
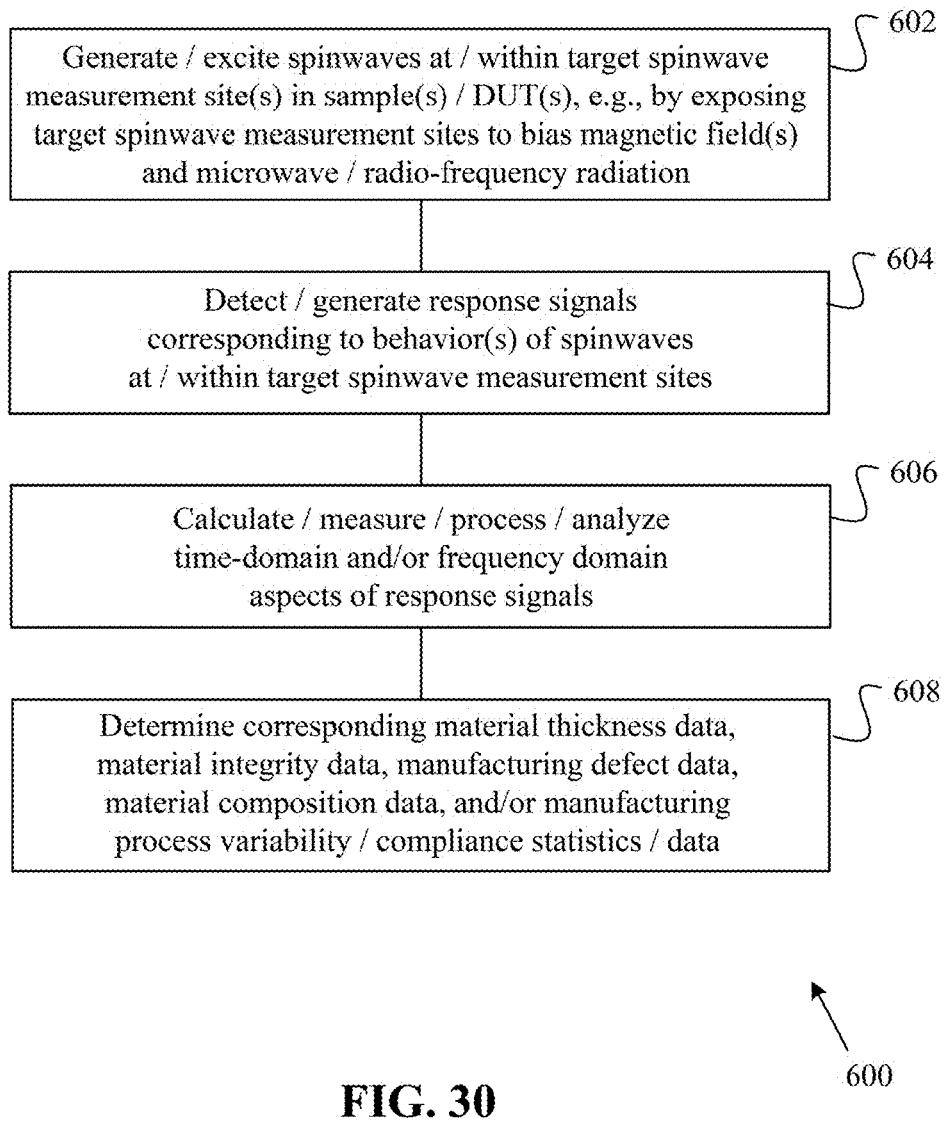
FIG. 30 is a flow diagram of a process for making spinwave-based measurements in accordance with an embodiment of the present disclosure.

FIG. 30 is a flow diagram of a spinwave-based measurement process 600 in accordance with an embodiment of the present disclosure. In an embodiment, the process 600 includes a first process portion 602 involving generating or exciting spinwaves at or within a set of target spinwave measurement sites in one or more samples or DUTs under consideration. The first process portion 602 can involve the application or delivery of microwave, radio frequency radiation, and/or other frequency radiation to one or more target spinwave measurement sites by way of patterned or integrated structures, such as waveguides or transmission lines. Such patterned or integrated structures can have micron-size and/or nanometer-size characteristic dimensions (e.g., micron-scale or nanometer-scale characteristic feature geometries or minimum linewidths), and can be fabricated by way of microfabrication/microscale fabrication techniques and/or nanofabrication/nanoscale fabrication techniques, for instance, integrated circuit manufacturing techniques (e.g., one or more of photolithography, e-beam lithography, material deposition or coating processes, and material removal or etching processes) understood by one of ordinary skill in the relevant art.

The first process portion 602 can also involve establishing an appropriate relative positioning between a set of target sample or DUT spinwave measurement sites under consideration and a bias magnetic field and microwave or radio frequency radiation used to generate spinwaves. Such appropriate relative positioning can occur, for example, by way of controlled displacement of a sample or DUT with respect to a bias magnetic field unit and a microwave or radio frequency radiation source, such as a set of waveguides.

A second process portion 604 involves detecting or generating response signals corresponding to the behavior of spinwaves at/within the target sample or DUT spinwave measurement sites. In various embodiments, the second process portion 604 involves detecting one or more types of response signals by way of a set of waveguides.

A third process portion 606 involves calculating, measuring, analyzing, or processing time-domain and/or frequency-domain aspects of the response signals, and a fourth process portion 608 involves determining corresponding material or material structure thickness data, material or material structure integrity data, manufacturing process defect data, material or material structure composition data, and/or manufacturing process variability or compliance statistics or data.

Aspects of particular embodiments of the present disclosure address at least one aspect, problem, limitation, and/or disadvantage associated with exiting systems, apparatuses, circuits, and/or techniques for testing ferromagnetic materials, structures, components, or devices. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, apparatuses, components, processes, or alternatives thereof, may be desirably combined into other different systems, apparatuses, components, processes, and/or applications. In addition, various modifications, alterations, and/or improvements can be made to various embodiments by a person of ordinary skill in the art.

For instance, in some embodiments, spinwaves can be generated and/or detected in one or more manners other than the particular representative spinwave generation and/or detection manners described above. As a representative example, spinwaves can be generated or excited in a sample by way of an induction technique (e.g., involving a set of integrated waveguides, as described above), and one or more response signals corresponding to spinwave behavior(s) within the sample can be detected by way of Hall sensors. As another representative example, in certain embodiments, one or more sets of patterned structural elements for generating spinwaves or detecting spinwaves/spinwave-related effects can be carried by or fabricated within a sample itself. For instance, a sample can include a set of generator waveguide structures fabricated or integrated thereon/therein, and a spinwave detection apparatus or device (e.g., a set of detector waveguides) can remain external to the sample. Alternatively, a sample can include a set of detector waveguide structures fabricated or integrated thereon/therein, and a spinwave generation apparatus or device (e.g., a set of generator waveguides) can remain external to the sample.

Embodiments described in detail herein, the foregoing representative embodiment modifications/variations, and other embodiment modifications/variations are encompassed by the present disclosure and the scope of the following claims.

The invention claimed is:

1. A metrology method comprising:
   providing at least one sample;
   providing a bias magnetic field;
   generating radiation;
   concurrently exposing at least one target measurement site of the at least one sample to the bias magnetic field and the generated radiation to thereby excite spinwaves within the at least one target measurement site of the at least one sample;
   detecting a response signal corresponding to a behavior of the spinwaves excited within the at least one target measurement site of the at least one sample; and
   determining a presence of a manufacturing defect in the at least one sample corresponding to the behavior of the spinwaves within the at least one target measurement site of the at least one sample.

2. The metrology method of claim 1, further comprising determining a categorical type of manufacturing defect in the at least one sample corresponding to the behavior of spinwaves within the at least one target measurement site of the at least one sample.

3. The metrology method of claim 2, wherein the categorical type of manufacturing defect is one of a vertical line defect, a horizontal line defect, and a dot array defect.

4. The metrology method of claim 1, further comprising indicating a presence of an alignment error corresponding to one or more layers of the at least one sample.

5. The metrology method of claim 1, further comprising:
   identifying a distribution of detected response signals across the at least one sample;
   determining a manufacturing process statistic corresponding to the distribution of detected response signals across the at least one sample; and
   providing a visual representation of manufacturing process variations or manufacturing process errors correlated with the distribution of detected response signals across the at least one sample.

6. The metrology method of claim 1, wherein at least one of generating radiation and detecting the response signal occurs by way of a set of patterned waveguide elements fabricated in accordance with at least one of microfabrication techniques and nanofabrication techniques.

7. The metrology method of claim 6, wherein the set of patterned waveguide elements is positioned a predetermined separation distance away from the at least one sample, and wherein the at least one sample is displaceable relative to the set of patterned waveguide elements.

8. The metrology method of claim 6, wherein detecting the response signal comprises (i) detecting one of radiation transmitted through the at least one sample and radiation reflected by the at least one sample, or (ii) generating a voltage in the set of patterned waveguide elements by way of magnetic induction corresponding to the behavior of spinwaves within the at least one target measurement site of the at least one sample.

9. The metrology method of claim 6, wherein generating radiation occurs by way of a first set of patterned waveguide elements, and wherein detecting the response signal occurs by way of a second set of patterned waveguide elements.

10. The metrology method of claim 9, wherein the first set of patterned waveguide elements and the second set of patterned waveguide elements are one of physically distinct and physically non-distinct.

11. The metrology method of claim 6, wherein the set of patterned waveguide elements comprises multiple generator waveguide elements fabricated in an array and configured for generating radiation to facilitate exposure of multiple target measurement sites of the at least one sample to generated radiation on a sequential or a simultaneous basis.

12. The metrology method of claim 11, wherein the at least one sample comprises multiple devices under test (DUT), and wherein concurrently exposing at least one target measurement site of the at least one sample to the bias magnetic field and the generated radiation comprises exposing each DUT to the bias magnetic field and generated radiation to thereby excite spinwaves in each DUT.

13. The metrology method of claim 6, wherein the set of patterned waveguide elements comprises multiple detector waveguide elements fabricated in an array and configured for detecting multiple response signals corresponding to the behavior of spinwaves excited in multiple target measurement sites of the at least one sample on a sequential or simultaneous basis.

14. The metrology method of claim 13, wherein the at least one sample comprises multiple devices under test (DUT), and wherein detecting a response signal corresponding to a behavior of the spinwaves excited within the at least one target measurement site comprises detecting a response signal in each DUT.

15. A metrology system comprising:
a bias magnetic field unit configured for providing a set of bias magnetic fields;
a radiation generation apparatus configured for providing radiation within at least one spatial spinwave generation region;
a sample stage configured for carrying at least one sample such that a target measurement site of the at least one sample is positionable within the at least one spatial spinwave generation region;
a response signal generation apparatus configured for generating a response signal corresponding to a behavior of spinwaves generated within the target measurement site of the at least one sample; and
a processing unit configured for determining a presence of a manufacturing defect in the at least one sample corresponding to the behavior of the spinwaves within the target measurement site of the at least one sample.

16. The metrology system of claim 15, wherein the processing unit is further configured for determining at least one of (i) a categorical type of manufacturing defect in the at least one sample corresponding to the behavior of spinwaves within the target measurement site of the at least one sample, and (ii) a presence of an alignment error corresponding to one or more layers of the at least one sample.

17. The metrology system of claim 16, wherein the categorical type of manufacturing defect is one of a vertical line defect, a horizontal line defect, and a dot array defect.

18. The metrology system of claim 17, wherein at least one of the radiation generation apparatus and the response signal generation apparatus comprises a set of waveguide elements fabricated in accordance with at least one of microfabrication techniques and nanofabrication techniques.

19. The metrology system of claim 18, wherein the set of patterned waveguide elements is positioned a predetermined separation distance away from the sample stage, and wherein the sample stage is displaceable relative to the set of patterned waveguide elements.

20. The metrology system of claim 18, wherein each of the radiation generation apparatus and the response signal generation apparatus comprises a set of patterned waveguide elements.

21. The metrology system of claim 20, wherein the patterned waveguide elements corresponding to the radiation generation apparatus and the patterned waveguide elements corresponding to the response signal generation apparatus are one of physically distinct and physically non-distinct.

22. The metrology system of claim 18, wherein the set of patterned waveguide elements comprises multiple generator waveguide elements fabricated in an array and configured for generating radiation to facilitate exposure of multiple target measurement sites of the at least one sample to generated radiation on a sequential or a simultaneous basis.

23. The metrology system of claim 22, wherein the at least one sample comprises multiple devices under test (DUT), and wherein the system is configured for exposing each DUT to a bias magnetic field and generated radiation to thereby excite spinwaves in each DUT.

24. The metrology system of claim 18, wherein the set of patterned waveguide elements comprises multiple detector waveguide elements fabricated in an array and configured for detecting multiple response signals corresponding to the behavior of spinwaves excited in multiple target measurement sites of the at least one sample on a sequential or simultaneous basis.

25. The method of claim 17, wherein the at least one sample comprises multiple devices under test (DUT), and wherein the system is configured for detecting a response signal corresponding to the behavior of spinwaves excited in each DUT.

* * * * *